United States Patent
Bhattacharyya et al.

(10) Patent No.: US 8,173,794 B2
(45) Date of Patent: May 8, 2012

(54) COMPOSITIONS AND METHODS FOR ENHANCING DISEASE RESISTANCE IN PLANTS

(75) Inventors: Madan K. Bhattacharyya, Ames, IA (US); Shan Li, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 233 days.

(21) Appl. No.: 12/492,974

(22) Filed: Jun. 26, 2009

(65) Prior Publication Data

US 2010/0122375 A1 May 13, 2010

Related U.S. Application Data

(60) Provisional application No. 61/110,510, filed on Oct. 31, 2008.

(51) Int. Cl.
*C12N 15/29* (2006.01)
*C12N 15/52* (2006.01)
*C12N 15/82* (2006.01)
*A01H 5/00* (2006.01)

(52) U.S. Cl. ...... 536/23.6; 536/23.2; 800/279; 800/286; 800/298; 435/320.1

(58) Field of Classification Search ............... None
See application file for complete search history.

(56) References Cited

U.S. PATENT DOCUMENTS

2004/0031072 A1* 2/2004 La Rosa et al. ............... 800/278

OTHER PUBLICATIONS

Azevedo et al. The U-box protein family in plants (2001) Trends in plant science. 6: 354-358.*
Zheng et al. Spotted leaf11, a negative regulator of plant cell death and defense, encodes a U-Box/Armafillo repeat protein endowed with E3 ubiquitun ligase activity (2004) The Plant Cell 16: 2795-2080.*
Trujillo et al. Negative regulation of PAMP-triggered immunity by an E3 ubiquitin ligase triplet in Arabidopsis (2008) Current Biology 18: 1396-1401.*
Zeng, Li-Rong, et al., "Spotted leaf11, a Negative Regulator of Plant Cell Death and Defense, Encodes a U-Box/Armadillo Repeat Protein Endowed with E3 Ubitquitin Ligase Activity", The Plant Cell, vol. 16, pp. 2795-2080, Oct. 2004, 2004 American Society of Plant Biologists.
Trujillo, Marco, et al., "NEgative Regulation of PAMP-Triggered Immunity by an E3 Ubiquitin Ligase Triplet in Arabidopsis", Current Biology 18, pp. 1396-1401, Sep. 23, 2008, Elsevier Ltd.

* cited by examiner

*Primary Examiner* — Russell Kallis
*Assistant Examiner* — Steven Bernacki
(74) *Attorney, Agent, or Firm* — McKee, Voorhees & Sease, P.L.C.

(57) ABSTRACT

Compositions and methods for enhancing disease resistance in plants by modulating levels or activities of GmUBox1 polynucleotides and polypeptides are provided. Transformed plants, plant cells, tissues, and seed are also provided having enhanced disease resistance.

9 Claims, 9 Drawing Sheets

Figure 2:
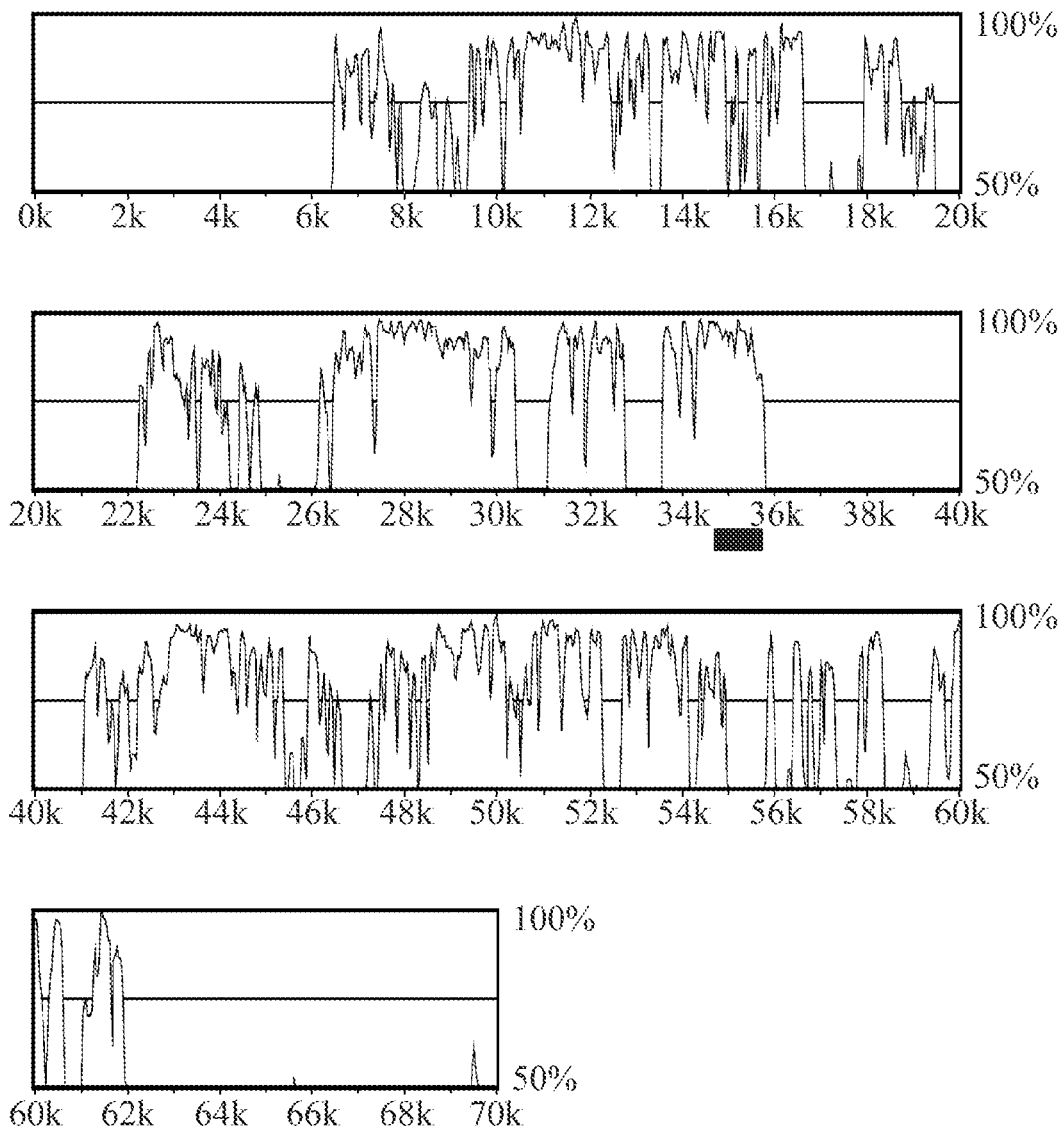

>GmUBox1-1
ATGGATGAAATTGAAATCCCTGCTCATTTCCTCTGCCCCATTTCCCTCCAACTCATGAGGGACCCTGTCACGGTTTGCAC
AGGAATCACTTAGTGATAGAGAGAACATAGAGAGATGGTTATTTTCATGCAAGAACAACACATGCCCCGTTACTAAGCAGT
GTCTATTaaaccatgatctcacccCAAACCACACTCTACGGAGGTTGATCCAATCTTGGTGCACCCTCAACGCCTCTCTA
GGAGTTGAACGCATTCCAACTCCAAAGTCACCAATAGACAGAACTCAGATTGTGAAACTCCTCACAGAAGCAAAAAGGTT
CCCTGAGAAGCAACTCAAGTGCCTCACAAGGCTTCGATCCATTGCCTTTGAAGGCCAAAGGAACAAAACATGTTTAGAGT
CTGCAGGAGTAATAGAATTCTTGGTCTCAACAATGAAGAACAACAACACACAAGAAGACTCAACTGTTCTCAGTGAAGCA
GCTATTGAAGTCTTGTTCCACCTCAATCTTTCCGAGGCTCGGGTTAAAGCTCTGATTAACAACGAGGAATTTCATTTTAT
TGAGTCATTgtttcatgttttaagaCTTGGAAACTACCAATCTAGAGCCTTTGCTACAATGCTGCTTAGATCAGCATTTG
AGGTAGCTGatccaatccaattgatCAGTGTCAAAACTGCACTGTCGTGGAAATCATGCGCGTTCTGCGCGATCAGATT
TCGCAGCAGGCTTCAAAGGCTGCATTGAAGCTCATTGTGGAGCTCTTTCCGTGGGGAAGAAACAGGATCAAAGGGGTTGA
GGGTGGTGCTGTTTTGGTCCTCGTTGAGTTACTTCTTGGTGCCCTCGGAAAGAAGAACGTGTGAACTCATTTTGATAGCTT
TGGATCAGCTTTGTGGGTGTGCAGAAGGGCGTGCAGAGTTGTTGAACCATGGAGCAGGAGTGGCCATTGTGTCCAAGAAA
ATTCTAAGGGTCTCTCATGTGGCAAGTGACAGAGGGGTTAGAATTTTAGCCTCTATTTGTAGGTATTCCGCCAATGCTAG
AGTGCTTCATGAAATGTTGCAGGTTGGGGCAGTGTCCAAGTTGTGCTTGGTGCTTCAAGTGAATTGCAGTTTAAAGACTA
AGGAGAGCGCAAAGGAAATACTCCAATTGCATTCTGTGGTTTGGAAGAATTCTCCATGTATTCCTGTACCTTTGTTATC
TTCCTATCCATGA (SEQ ID NO:1)

>GmUBox1-2
ATGGACGAAATTGAAATCCCTGCCCATTTCCTCTGCCCCATTTCCCTTCAACTCATGAGGGACCCTGTCACGGTTTGCAC
AGGAATCACTTATGATAGAGAAAACATAGAGAGATGGTTATTTTCATGCAAGAACAACACATGCCCCGTTACTAAGCAGT
GCCTATTAGACCATGGTCTCACTCCAAACCACACTCTACGCAGGCTGATCCAATCCTGGTGCACCCTCAATGCCTCACTT
GGAGTTGAACGCATTCCTACTCCAAAGTCACCAATAGACAAAACTCAGATTGTGAAACTCCTCACAGAAGCAAAAAGGTT
CCCTGAGAAGCAACTCAAGTGCCTCACAAGGCTTCGATCCGTTGCCTTTGAAGGCCAAAGGAACAAAACATGTTTAGAGT
CTGCTGGAGTAATAGAATTCTTGGCCACAACAATGAAGAACAACAACACACAAGAAGACTCAACTGTTCTCAGTGAAGCA
GCTATTGAAGTCTTGTTCCACCTCAATCTCTCCGAGGCTCGACTTAAAACTCTGATTAACAACGAGGAATTTCATTTTAT
CGAGTCATTGTTTCATGTGCTGAGGCTTGGAAACTACCAATCTAGAGTCTATGCTACAATGCTGCTTAGATCAGCATTTG
AGGTAGCTGATCCAATCCAATTGATCAGTGTCAAAACCGGCGCTGTTTGTGGAAATCATGCGCGTGCTTTGCGATCAGATC
TCGCATCAGCCTTCAAAGGCTGCATTGAAGCTCATTGTGAGCCTCTTTCCGTGGGAAGAAACACGATCAAAGGGCTCGA
GGATGGTACAGTTTCGGTCCTCATCGAGCTACTTCTCGGCACCTCGGAAAGAAGAACATGTGAACTCATTTTGATAGCTT
TGGATCAGCTTTGTGGGTGTGCAGAAGGGCGTGCAGAGTTGTTGAACCATGGGGCAGGAGTGGCCATTGTGTCCAAGAAA
ATTCTAAGGGTCTCTCATGTGGCTAGTGAAAGAGGGGTTAGAATTTTGGCCTCTATTTGTAGGTATTCTGCCAATGCTAG
AGTGCTTCATGAAATGTTGCAGGTTGGGCTGTGTCCAAGTTGTGTTTGGTGCTTCAAGTGAATTGCGGTTTAAAGACTA
AGGAGAGAGCCAAAGAGGTACTCAAATTGCACTCGGTGGTTTGGAAGAATTCCCCATGTATTCCTGTACCTTTGTTATCT
TCCTATCCATGA (SEQ ID NO:2)

```
GmUBox1-1      MDEIEIPAHFLCPISLQLMRDPVTVCTGITYDRENIERWLFSCKNNTCPVTKQCLLNHDL  60
GmUBox1-2      MDEIEIPAHFLCPISLQLMRDPVTVCTGITYDRENIERWLFSCKNNTCPVTKQCLLDHGL  60
               ************************************************::.*

GmUBox1-1      TPNHTLRRLIQSWCTLNASLGVERIPTPKSPIDRTQIVKLLTEAKRFPEKQLKCLTRLRS  120
GmUBox1-2      TPNHTLRRLIQSWCTLNASLGVERIPTPKSPIDKTQIVKLLTEAKRFPEKQLKCLTRLRS  120
               *********************************:**************************

GmUBox1-1      IAFEGQRNKTCLESAGVIEFLVSTMKNNNTQEDSTVLSEAAIEVLFHLNLSEARVKALIN  180
GmUBox1-2      VAFEGQRNKTCLESAGVIEFLATTMKNNNTQEDSTVLSEAAIEVLFHLNLSEARLKTLIN  180
               :********************::************************:*:***

GmUBox1-1      NEEFHFIESLFHVLRLGNYQSRAFATMLLRSAFEVADPIQLISVKTALFVFIMRVLRDQT  240
GmUBox1-2      NEEFHFIESLFHVLRLGNYQSRVYATMLLRSAFEVADPIQLISVKTALFVEIMRVLCDQI  240
               **********************: **********************:*****  ** *

GmUBox1-1      SQQASKAALKLIVELFPWGRNRIKGVEGGAVLVLELLLGASERRTCELILIALDQLCGC  300
GmUBox1-2      SHQASKAALKLIVELFPWGRNRIKGVEDGTVSVLIELLLGTSERRTCELILIALDQLCGC  300
               *:*************************: * **:*****.*******************

GmUBox1-1      AEGRAELLNHGAGVAIVSKKILRVSHVASDRGVRILASICRYSANARVLHEMLQVGAVSK  360
GmUBox1-2      AEGRAELLNHGAGVAIVSKKILRVSHVASERGVRILASICRYSANARVLHEMLQVGAVSK  360
               *****************************:******************************

GmUBox1-1      LCLVLQVNCSLKTKERAKEILQLHSVVWKNSPCIPVPLLSSYP  403 (SEQ ID NO:3)
GmUBox1-2      LCLVLQVNCGFKTKERAKEVLKLHSVVWKNSPCIPVPLLSSYP  403 (SEQ ID NO:4)
               *********. :******* *:*********************
```

Figure 1

D
```
MDEIEIPAHF LCPISLQLMR DPVTVCTGIT YDRENIERWL FSCKNNTCPV TKQCLLNHDL
TPNHTLRRLI QSWCTLNASL GVERIPTPKS PIDRTQIVKL LTEAKRFPEK QLKCLTRLRS
IAFEGQRNKT CLESAGVIEF LVSTMKNNNT QEDSTVLSEA AIEVLFHLNL SEARVKALIN
NEEFHFIESL FHVLRLGNYQ SRAFATMLLR SAFEVADPIQ LISVKTALFV EIMRVLRDQI
SQQASKAALK LIVELFPWGR NRIKGVEGGA VLVLVELLLG ASERRTCELI LIALDQLCGC
AEGRAELLNH GAGVAIVSKK ILRVSHVASD RGVRILASIC RYSANARVLH EMLQVGAVSK
LCLVLQVNCS LKTKERAKEI LQLHSVVWKN SPCIPVPLLS SYP (SEQ ID NO:3)
```

E
```
MDEIEIPAHF LCPISLQLMR DPVTVCTGIT YDRENIERWL FSCKNNTCPV TKQCLLDHGL
TPNHTLRRLI QSWCTLNASL GVERIPTPKS PIDKTQIVKL LTEAKRFPEK QLKCLTRLRS
VAFEGQRNKT CLESAGVIEF LATTMKNNNT QEDSTVLSEA AIEVLFHLNL SEARLKTLIN
NEEFEFIESL FHVLRLGNYQ SRVYATMLLR SAFEVADPIQ LISVKTALFV EIMRVLCDQI
SHQASKAALK LIVELFPWGR NRIKGVEDGT VSVLIELLLG TSERRTCELI LIALDQLCGC
AEGRAELLNH GAGVAIVSKK ILRVSHVASE RGVRILASIC RYSANARVLH EMLQVGAVSK
LCLVLQVNCG FKTKERAKEV LKLHSVVWKN SPCIPVPLSS SYP (SEQ ID NO:4)
```

Figure 1 (Continued)

```
PUB22       ------------------------------------------------------------
PUB23       ------------------------------------------------------------
GmUBox1-1   ------------------------------------------------------------
GmUBox1-2   ------------------------------------------------------------
PUB24       ------------------------------------------------------------
SPL11       MAGDRAEEEEGEAPPPEARAAAAVERVAAAVEAVAAGAGAGAGEYRNAYRRQLLALSRRI 60

PUB22       ------------------------------------------------------------
PUB23       ------------------------------------------------------------
GmUBox1-1   ------------------------------------------------------------
GmUBox1-2   ------------------------------------------------------------
PUB24       ------------------------------------------------------------
SPL11       RLLGPFVEELRERPRGEGEGEEEERALAPLADALEAALALLRLGPEGSRISLVLERDSVM 120

PUB22       ------------------------------------------------------------
PUB23       ------------------------------------------------------------
GmUBox1-1   ------------------------------------------------------------
GmUBox1-2   ------------------------------------------------------------
PUB24       ------------------------------------------------------------
SPL11       KKFQGVILQLEQALCDIPYNELDISDEVREQVELVHAQLKRAKERIDMPDDEFYNDLLSV 180

PUB22       ------------------------------------------------------------
PUB23       ------------------------------------------------------------
GmUBox1-1   ------------------------------------------------------------
GmUBox1-2   ------------------------------------------------------------
PUB24       ------------------------------------------------------------
SPL11       YDKNYDPSAELAILGRLSEKLHLMTITDLTQESLALHEMVASGGGQDPGEHIERMSMLLK 240

PUB22       -------------------------MDQEIEIPSFFLCPISLDIMKDPVIVSTGITYDR 34
PUB23       --------------------MSGGIMDEEIEIPPFFLCPISLEIMKDPVIVSTGITYDR 39
GmUBox1-1   -------------------------MDEIEIPAHFLCPISLQLMRDPVTVCTGITYDR 33
GmUBox1-2   -------------------------MDEIEIPAHFLCPISLQLMRDPVTVCTGITYDR 33
PUB24       -----------------------MDQEEEEIEIPNYFICPISLEIMKDPVTTVSGITYDR 37
SPL11       KIKDFVQTQNPDMGPFMASRVLDSNGDSRPITIPDEFRCPISLELMKDPVIVSTGQTYER 300
                                       *  **    * *****::*:***   :* **:*

PUB22       ESIEKWLFSGKKNSCPVTKQVI-TETDLTPNHTLRRLIQSWCTLNASYGIERIPTPKPFI 93
PUB23       DSIEKWLFAGKKNSCPVTKQDI-TDADLTPNHTLRRLIQSWCTLNASYGVERIPTPRPPI 98
GmUBox1-1   ENIERWLFSCKNNTCPVTKQCL-LNHDLTPNHTLRRLIQSWCTLNASLGVERIPTPKSPI 92
GmUBox1-2   ENIERWLFSCKNNTCPVTKQCL-LDHGLTPNHTLRRLIQSWCTLNASLGVERIPTPKSPI 92
PUB24       QNIVKWLEKVP--SCPVTKQPLPLDSDLTPNHMLRRLIQHWCVENETRGVVRISTPPVPP 95
SPL11       ACIEKWIASGH-HTCPTTTQQKM-STSALTPNYVLRSLISQWCETNGMEPPKRSTQPNKPT 358
              * :*:      :**.*:*  :     ****: ** **.**  *     *   *.  *

PUB22       ------CKSEIEKLIKESSSS---HLNQVKCLKRLRQIVSENTTNKRCLEAAEVPEFLAN 144
PUB23       ------CKSEIEKLIPDSASS---HENQVKCLKRLRQIVSENATNKRCLEAACVPEFLAN 149
GmUBox1-1   ------DKTQIVKLLTEAKRF---PEKQLKCLTRLESIAFEGQRNKTCLESAGVIEFLVS 143
GmUBox1-2   ------DKTQIVKLLTEAKRF---PEKQLKCLTRLRSVAFEGQRNKTCLESAGVIEFLAT 143
PUB24       ------GKLNVVEEIKNLKKFGQEALGREETLQKLEVLAMDGNNERIMCECGVHKSLILF 149
SPL11       PACSSSERANIDALLSKLCSP--DTEEQRSAAAELRLLAKRNANNPRICIAEAGAIPLLLS 416
                  :  ::    :.        :  .   .*. :.  ..          ::

PUB22       IVSNSVDTYNSPSSSLSSSNLNDMCQSNMLENRFDSSRSLMDEALSVLYHLDTSETALKS 204
PUB23       IVSN--DSENG---------------------------SLTDEALNLLYHLETSETVLKN 180
GmUBox1-1   TMKNNNTQEDS--------------------------TVLSEAAIEVLFHLNLSEARVKA 177
GmUBox1-2   TMKNNNTQEDS--------------------------TVLSEAAIEVLFHLNLSEARLKT 177
PUB24       VVKCTSEDEDG--------------------------RRRIKGLDESLRLLHLIGIFSNDAKT 186
SPL11       LLSSS-----------------------------DLRTQEHAVTALLNLSIHEDNKAS 445
              :.                             :  ::    *   :   .

PUB22       LLNNKKGTNLVKTLTKIMQRGIYESRAYAALLLKKLLEVADPMQIILLEBELFGEVIQIL 264 (SEQ ID NO:8)
PUB23       LLNNKKDNNIVKSLTKIMQRGPMYESPVYATLLLKNILEVADPMQSMTLKPEVFTEVVQIL 240 (SEQ ID NO:9)
GmUBox1-1   LINNEE-FHFIESLFHVLRLGNYQSRAFATMLLRSAFEVADPIQLISVKTALFVEIMRVL 236 (SEQ ID NO:10)
GmUBox1-2   LINNEE-FHFIESLFHVLRLGNYQSRVYATMLLRSAFEVADPIQLISVKTALFVEIMRVL 236 (SEQ ID NO:11)
PUB24       ILMEND--RVMESLTWVLHQEDFLSKAYTIVLLRNLTEYTSSHIVERLNPEIFKGIIGFL 244 (SEQ ID NO:12)
SPL11       IISSGA----VPSIVHVLKNGSMEARENAAATLFSLSVIDEYKVTIGGMGAIPALVVLLG 501 (SEQ ID NO:13)
            ::  .      : ::  ::       ::  *  .   .   :  :      :  .
```

Figure 3

A  CAATCTTGGTGCACCCTCAACGCCTCTCTAGGAGTTGAACGCATTCCAACTCCAAAGTCA
CCAATAGACAGAACTCAGATTGTGAAACTCCTCACAGAAGCAAAAAGGTTCCCTGAGAAG
CAACTCAAGTGCCTCACAAGGCTTGATCCATTGCCTTTGAAGGCCAAAGGAACAAAACA
TGTTTAGAGTCTCCACCAGTAATACAATTCTTCGTCTCAACAATGAAGAACAACAACACA
CAAGAAGACTCAACTGTTCTCAGTGAAGCAGCTATTGAAGTCTTGTTCCACCTCAATCTT
TCCGAGGCTCGGGTTAAAGCTCTGATTAACAACGAGGAATTTCATTTTATTGAGTCATTG
TTTCATGTTTTAAGACTTGGAAACTACCAATCTAGAGCCTTTGCTACAATGCTGCTTAGA
TCAGCATTTGAGGTAGCTGATCCAATCCAATTGATCAGTGTCAAAACTGCACTGTTCGTG
GAAATCATGCGCGTTCTGCGCGATCAGATTTCGCAGCAGGCTTCAAAGGCTGCATTGAAG
CTCATTGTGGAGCTCTTTCCGTGGGGAAGAAACAGGATCAAAGGGGTTGAGGGTGGTGCT
GTTTTGGTCCTCGTTGAGTTACTTCTTGGTGCCTCGGAAAGAAGAACGTGTGAACTCATT
TTGATAGCTTTGGATCAGCTTTGTGGGTGTGCAGAAGGGCGTGCAGAGTTGTTGAACCAT
GGAGCAGGAGTGGCCATTGTGTCCAAGAAAATTCTAAGGGTCTCTCATGTGGCAAGTGAC
AGAGGGGTTAGAATTTTAGCCTCTATTTGTAGGTATTCCGCCAATGCTAGAGTGCTTCAT
GAAATGTTGCAGGTTGGGGCAGTGTCCAAGTTGTGCTTGGTGCTTCAAGTGAATTGCAGT
TTAAAGACTAAGGAGAGGGCAAAGGAAATACTCCAATTGCATTCTGTGGTTTGGAAGAAT
TCTCCATGTATTCCTGTACCTTTGTTATCTTCCTATCCATGA (SEQ ID NO:5)

B  QSWCTLNASLGVERIPTPKSXIDRTQIVKLLTEAKRFPEKQLKCLTRLKSIAFEGQRNKTCLESAGVI
EFLVSTMKNNNTQEDSTVLSEAAIEVLFHLNLSEARVKALINNEEFHFIESLFHVLRIGNYQSKAFAT
MLLRSAFEVADPIQLISVKTALFVEIMRVLRDQISQQASKAALKLIVELFPWGRNRIKGVEGGAVLVL
VELLLGASERRTCELILIALDQLCCCAECRAELLNHCAGVAIVSKKILRVSHVASDRGVRILASICRY
SANARVLHEMLQVGAVSKLCLVLXVNCSLKTKERAKE (SEQ ID NO:6)

Figure 7

GCCTTTGCTACAATGCTGCTTAGATCAGCATTTGAGGTAGCTGatccaatccaattgatCAGTGTCAAAACTGCACTGTT
CGTGGAAATCATGCGCGTTCTGCGCGATCAGATTTCGCAGCAGGCTTCAAAGGCTGCATTGAAGCTCATTGTGGAGCTCT
TTCCGTGGGGAAGAAACAGGATCAAAGGGGTTGAGGGTGGTGCTGTTTTGGTCCTCGTTGAGTTACTTCTTGGTGCCTCG
GAAAGAACAACGTCTGAACTCATTTTCATAGCTTTGGATCAGCTTTGTCGGTGTGCAGAACGGCCTGCAGAGTTGTTCAA
CCATGGAGCAGGAGTGGCCATTGTGTCCAAGAAAATTCTAAGGGTCTCTCATGTGGCAAGTGACAGAGGGGTTAGAATTT
TAGCCTCTATTTG TAGGTATTCCGCCAATGCTAGAGTG (SEQ ID NO:7)

Figure 8

SEQUENCE LISTING

```
<160> NUMBER OF SEQ ID NOS: 19

<210> SEQ ID NO 1
<211> LENGTH: 1212
<212> TYPE: DNA
<213> ORGANISM: Glycine max

<400> SEQUENCE: 1
atggatgaaa ttgaaatccc tgctcatttc ctctgcccca tttccctcca actcatgagg      60
gaccctgtca cggtttgcac aggaatcact tatgatagag agaacataga gagatggtta     120
ttttcatgca agaacaacac atgccccgtt actaagcagt gtctattaaa ccatgatctc     180
accccaaacc acactctacg gaggttgatc caatcttggt gcaccctcaa cgcctctcta     240
ggagttgaac gcattccaac tccaaagtca ccaatagaca gaactcagat tgtgaaactc     300
ctcacagaag caaaaaggtt ccctgagaag caactcaagt gcctcacaag gcttcgatcc     360
attgcctttg aaggccaaag gaacaaaaca tgtttagagt ctgcaggagt aatagaattc     420
ttggtctcaa caatgaagaa caacaacaca caagaagact caactgttct cagtgaagca     480
```

-continued

```
gctattgaag tcttgttcca cctcaatctt tccgaggctc gggttaaagc tctgattaac    540
aacgaggaat tcattttat tgagtcattg tttcatgttt aagacttgg aaactaccaa     600
tctagagcct tgctacaat gctgcttaga tcagcatttg aggtagctga tccaatccaa    660
ttgatcagtg tcaaaactgc actgttcgtg gaaatcatgc gcgttctgcg cgatcagatt   720
tcgcagcagg cttcaaaggc tgcattgaag ctcattgtgg agctcttttcc gtggggaaga  780
aacaggatca aaggggttga gggtggtgct gttttggtcc tcgttgagtt acttcttggt   840
gcctcggaaa aagaacgtg tgaactcatt ttgatagctt tggatcagct ttgtgggtgt    900
gcagaagggc gtgcagagtt gttgaaccat ggagcaggag tggccattgt gtccaagaaa   960
attctaaggg tctctcatgt ggcaagtgac agagggggtta gaattttagc ctctatttgt  1020
aggtattccg ccaatgctag agtgcttcat gaaatgttgc aggttggggc agtgtccaag   1080
ttgtgcttgg tgcttcaagt gaattgcagt ttaaagacta aggagagggc aaaggaaata   1140
ctccaattgc attctgtggt ttggaagaat tctccatgta ttcctgtacc tttgttatct   1200
tcctatccat ga                                                        1212

<210> SEQ ID NO 2
<211> LENGTH: 1212
<212> TYPE: DNA
<213> ORGANISM: Glycine max

<400> SEQUENCE: 2
atggacgaaa ttgaaatccc tgcccatttc ctctgcccca tttcccttca actcatgagg     60
gaccctgtca cggtttgcac aggaatcact tatgatagag aaaacataga gagatggtta    120
ttttcatgca agaacaacac atgccccgtt actaagcagt gcctattaga ccatggtctc    180
actccaaacc acactctacg caggctgatc caatcctggt gcaccctcaa tgcctcactt    240
ggagttgaac gcattcctac tccaaagtca ccaatagaca aaactcagat tgtgaaactc    300
ctcacagaag caaaaaggtt cccagagaag caactcaagt gcctcacaag gcttcgatcc    360
gttgcctttg aaggccaaag gaacaaaaca tgtttagagt ctgctggagt aatagaattc    420
ttggccacaa caatgaagaa caacaacaca caagaagact caactgttct cagtgaagca    480
gctattgaag tcttgttcca cctcaatctc tccgaggctc gacttaaaac tctgattaac    540
aacgaggaat tcattttat cgagtcattg tttcatgtgc tgaggcttgg aaactaccaa     600
tctagagtct atgctacaat gctgcttaga tcagcatttg aggtagctga tccaatccaa    660
ttgatcagtg tcaaaaccgc gctgtttgtg gaaatcatgc gcgtgctttg cgatcagatc    720
tcgcatcagg cttcaaaggc tgcattgaag ctcattgtgg agctcttttcc gtggggaaga  780
aacaggatca aaggggtcga ggatggtaca gtttcggtcc tcatcgagct acttctcggc    840
acctcggaaa aagaacatg tgaactcatt ttgatagctt tggatcagct ttgtgggtgt    900
gcagaagggc gtgcagagtt gttgaaccat ggggcaggag tggccattgt gtccaagaaa   960
attctaaggg tctctcatgt ggctagtgaa agagggggtta gaattttggc ctctatttgt  1020
aggtattctg ccaatgctag agtgcttcat gaaatgttgc aggttggggc tgtgtccaag   1080
ttgtgtttgg tgcttcaagt gaattgcggt tttaagacta aggagagagc caaagaggta   1140
ctcaaattgc actcggtggt ttggaagaat tccccatgta ttcctgtacc tttgttatct   1200
tcctatccat ga                                                        1212

<210> SEQ ID NO 3
<211> LENGTH: 403
```

```
<212> TYPE: PRT
<213> ORGANISM: Glycine max

<400> SEQUENCE: 3

Met Asp Glu Ile Glu Ile Pro Ala His Phe Leu Cys Pro Ile Ser Leu
1               5                   10                  15

Gln Leu Met Arg Asp Pro Val Thr Val Cys Thr Gly Ile Thr Tyr Asp
            20                  25                  30

Arg Glu Asn Ile Glu Arg Trp Leu Phe Ser Cys Lys Asn Thr Cys
        35                  40                  45

Pro Val Thr Lys Gln Cys Leu Leu Asn His Asp Leu Thr Pro Asn His
        50                  55                  60

Thr Leu Arg Arg Leu Ile Gln Ser Trp Cys Thr Leu Asn Ala Ser Leu
65                  70                  75                  80

Gly Val Glu Arg Ile Pro Thr Pro Lys Ser Pro Ile Asp Arg Thr Gln
                85                  90                  95

Ile Val Lys Leu Leu Thr Glu Ala Lys Arg Phe Pro Glu Lys Gln Leu
            100                 105                 110

Lys Cys Leu Thr Arg Leu Arg Ser Ile Ala Phe Glu Gly Gln Arg Asn
        115                 120                 125

Lys Thr Cys Leu Glu Ser Ala Gly Val Ile Glu Phe Leu Val Ser Thr
        130                 135                 140

Met Lys Asn Asn Asn Thr Gln Glu Asp Ser Thr Val Leu Ser Glu Ala
145                 150                 155                 160

Ala Ile Glu Val Leu Phe His Leu Asn Leu Ser Glu Ala Arg Val Lys
                165                 170                 175

Ala Leu Ile Asn Asn Glu Glu Phe His Phe Ile Glu Ser Leu Phe His
            180                 185                 190

Val Leu Arg Leu Gly Asn Tyr Gln Ser Arg Ala Phe Ala Thr Met Leu
        195                 200                 205

Leu Arg Ser Ala Phe Glu Val Ala Asp Pro Ile Gln Leu Ile Ser Val
        210                 215                 220

Lys Thr Ala Leu Phe Val Glu Ile Met Arg Val Leu Arg Asp Gln Ile
225                 230                 235                 240

Ser Gln Gln Ala Ser Lys Ala Ala Leu Lys Leu Ile Val Glu Leu Phe
                245                 250                 255

Pro Trp Gly Arg Asn Arg Ile Lys Gly Val Glu Gly Gly Ala Val Leu
            260                 265                 270

Val Leu Val Glu Leu Leu Leu Gly Ala Ser Glu Arg Arg Thr Cys Glu
        275                 280                 285

Leu Ile Leu Ile Ala Leu Asp Gln Leu Cys Gly Cys Ala Glu Gly Arg
        290                 295                 300

Ala Glu Leu Leu Asn His Gly Ala Gly Val Ala Ile Val Ser Lys Lys
305                 310                 315                 320

Ile Leu Arg Val Ser His Val Ala Ser Asp Arg Gly Val Arg Ile Leu
                325                 330                 335

Ala Ser Ile Cys Arg Tyr Ser Ala Asn Ala Arg Val Leu His Glu Met
            340                 345                 350

Leu Gln Val Gly Ala Val Ser Lys Leu Cys Leu Val Leu Gln Val Asn
        355                 360                 365

Cys Ser Leu Lys Thr Lys Glu Arg Ala Lys Glu Ile Leu Gln Leu His
        370                 375                 380

Ser Val Val Trp Lys Asn Ser Pro Cys Ile Pro Val Pro Leu Leu Ser
385                 390                 395                 400
```

Ser Tyr Pro

<210> SEQ ID NO 4
<211> LENGTH: 403
<212> TYPE: PRT
<213> ORGANISM: Glycine max

<400> SEQUENCE: 4

```
Met Asp Glu Ile Glu Ile Pro Ala His Phe Leu Cys Pro Ile Ser Leu
1               5                   10                  15

Gln Leu Met Arg Asp Pro Val Thr Val Cys Thr Gly Ile Thr Tyr Asp
            20                  25                  30

Arg Glu Asn Ile Glu Arg Trp Leu Phe Ser Cys Lys Asn Asn Thr Cys
        35                  40                  45

Pro Val Thr Lys Gln Cys Leu Leu Asp His Gly Leu Thr Pro Asn His
    50                  55                  60

Thr Leu Arg Arg Leu Ile Gln Ser Trp Cys Thr Leu Asn Ala Ser Leu
65                  70                  75                  80

Gly Val Glu Arg Ile Pro Thr Pro Lys Ser Pro Ile Asp Lys Thr Gln
                85                  90                  95

Ile Val Lys Leu Leu Thr Glu Ala Lys Arg Phe Pro Glu Lys Gln Leu
            100                 105                 110

Lys Cys Leu Thr Arg Leu Arg Ser Val Ala Phe Glu Gly Gln Arg Asn
        115                 120                 125

Lys Thr Cys Leu Glu Ser Ala Gly Val Ile Glu Phe Leu Ala Thr Thr
    130                 135                 140

Met Lys Asn Asn Asn Thr Gln Glu Asp Ser Thr Val Leu Ser Glu Ala
145                 150                 155                 160

Ala Ile Glu Val Leu Phe His Leu Asn Leu Ser Glu Ala Arg Leu Lys
                165                 170                 175

Thr Leu Ile Asn Asn Glu Glu Phe His Phe Ile Glu Ser Leu Phe His
            180                 185                 190

Val Leu Arg Leu Gly Asn Tyr Gln Ser Arg Val Tyr Ala Thr Met Leu
        195                 200                 205

Leu Arg Ser Ala Phe Glu Val Ala Asp Pro Ile Gln Leu Ile Ser Val
    210                 215                 220

Lys Thr Ala Leu Phe Val Glu Ile Met Arg Val Leu Cys Asp Gln Ile
225                 230                 235                 240

Ser His Gln Ala Ser Lys Ala Ala Leu Lys Leu Ile Val Glu Leu Phe
                245                 250                 255

Pro Trp Gly Arg Asn Arg Ile Lys Gly Val Glu Asp Gly Thr Val Ser
            260                 265                 270

Val Leu Ile Glu Leu Leu Leu Gly Thr Ser Glu Arg Arg Thr Cys Glu
        275                 280                 285

Leu Ile Leu Ile Ala Leu Asp Gln Leu Cys Gly Cys Ala Glu Gly Arg
    290                 295                 300

Ala Glu Leu Leu Asn His Gly Ala Gly Val Ala Ile Val Ser Lys Lys
305                 310                 315                 320

Ile Leu Arg Val Ser His Val Ala Ser Glu Arg Gly Val Arg Ile Leu
                325                 330                 335

Ala Ser Ile Cys Arg Tyr Ser Ala Asn Ala Arg Val Leu His Glu Met
            340                 345                 350

Leu Gln Val Gly Ala Val Ser Lys Leu Cys Leu Val Leu Gln Val Asn
        355                 360                 365

Cys Gly Phe Lys Thr Lys Glu Arg Ala Lys Glu Val Leu Lys Leu His
```

```
                370                 375                 380
Ser Val Val Trp Lys Asn Ser Pro Cys Ile Pro Val Pro Leu Leu Ser
385                 390                 395                 400

Ser Tyr Pro

<210> SEQ ID NO 5
<211> LENGTH: 1002
<212> TYPE: DNA
<213> ORGANISM: Glycine max

<400> SEQUENCE: 5
caatcttggt gcaccctcaa cgcctctcta ggagttgaac gcattccaac tccaaagtca       60
ccaatagaca gaactcagat tgtgaaactc ctcacagaag caaaaaggtt ccctgagaag      120
caactcaagt gcctcacaag gcttcgatcc attgcctttg aaggccaaag gaacaaaaca      180
tgtttagagt ctgcaggagt aatagaattc ttggtctcaa caatgaagaa caacaacaca      240
caagaagact caactgttct cagtgaagca gctattgaag tcttgttcca cctcaatctt      300
tccgaggctc gggttaaagc tctgattaac aacgaggaat tcatttttat tgagtcattg      360
tttcatgttt taagacttgg aaactaccaa tctagagcct tgctacaat gctgcttaga       420 tcagcatttg aggtagctga tccaatccaa ttgatcagtg tcaaaactgc actgttcgtg      480
gaaatcatgc gcgttctgcg cgatcagatt tcgcagcagg cttcaaaggc tgcattgaag      540
ctcattgtgg agctctttcc gtggggaaga acaggatca aggggttga gggtggtgct        600 gttttggtcc tcgttgagtt acttcttggt gcctcggaaa gaagaacgtg tgaactcatt      660
ttgatagctt tggatcagct ttgtgggtgt gcagaagggc gtgcagagtt gttgaaccat      720
ggagcaggag tggccattgt gtccaagaaa attctaaggg tctctcatgt ggcaagtgac      780
agaggggtta gaattttagc ctctatttgt aggtattccg ccaatgctag agtgcttcat      840
gaaatgttgc aggttggggc agtgtccaag ttgtgcttgg tgcttcaagt gaattgcagt      900
ttaaagacta aggagagggc aaaggaaata ctccaattgc attctgtggt ttggaagaat      960
tctccatgta ttcctgtacc tttgttatct tcctatccat ga                       1002

<210> SEQ ID NO 6
<211> LENGTH: 309
<212> TYPE: PRT
<213> ORGANISM: Glycine max
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid

<400> SEQUENCE: 6

Gln Ser Trp Cys Thr Leu Asn Ala Ser Leu Gly Val Glu Arg Ile Pro
1               5                   10                  15

Thr Pro Lys Ser Xaa Ile Asp Arg Thr Gln Ile Val Lys Leu Leu Thr
            20                  25                  30

Glu Ala Lys Arg Phe Pro Glu Lys Gln Leu Lys Cys Leu Thr Arg Leu
        35                  40                  45

Arg Ser Ile Ala Phe Glu Gly Gln Arg Asn Lys Thr Cys Leu Glu Ser
    50                  55                  60

Ala Gly Val Ile Glu Phe Leu Val Ser Thr Met Lys Asn Asn Asn Thr
65                  70                  75                  80
```

```
Gln Glu Asp Ser Thr Val Leu Ser Glu Ala Ala Ile Glu Val Leu Phe
             85                  90                  95

His Leu Asn Leu Ser Glu Ala Arg Val Lys Ala Leu Ile Asn Asn Glu
            100                 105                 110

Glu Phe His Phe Ile Glu Ser Leu Phe His Val Leu Arg Leu Gly Asn
        115                 120                 125

Tyr Gln Ser Arg Ala Phe Ala Thr Met Leu Leu Arg Ser Ala Phe Glu
    130                 135                 140

Val Ala Asp Pro Ile Gln Leu Ile Ser Val Lys Thr Ala Leu Phe Val
145                 150                 155                 160

Glu Ile Met Arg Val Leu Arg Asp Gln Ile Ser Gln Gln Ala Ser Lys
                165                 170                 175

Ala Ala Leu Lys Leu Ile Val Glu Leu Phe Pro Trp Gly Arg Asn Arg
            180                 185                 190

Ile Lys Gly Val Glu Gly Gly Ala Val Leu Val Leu Val Glu Leu Leu
        195                 200                 205

Leu Gly Ala Ser Glu Arg Arg Thr Cys Glu Leu Ile Leu Ile Ala Leu
    210                 215                 220

Asp Gln Leu Cys Gly Cys Ala Glu Gly Arg Ala Glu Leu Leu Asn His
225                 230                 235                 240

Gly Ala Gly Val Ala Ile Val Ser Lys Lys Ile Leu Arg Val Ser His
                245                 250                 255

Val Ala Ser Asp Arg Gly Val Arg Ile Leu Ala Ser Ile Cys Arg Tyr
            260                 265                 270

Ser Ala Asn Ala Arg Val Leu His Glu Met Leu Gln Val Gly Ala Val
        275                 280                 285

Ser Lys Leu Cys Leu Val Leu Xaa Val Asn Cys Ser Leu Lys Thr Lys
    290                 295                 300

Glu Arg Ala Lys Glu
305

<210> SEQ ID NO 7
<211> LENGTH: 438
<212> TYPE: DNA
<213> ORGANISM: Artificial Sequence
<220> FEATURE:
<223> OTHER INFORMATION: sequence for generating RNAi for GmUBox
      sequences

<400> SEQUENCE: 7
gcctttgcta caatgctgct tagatcagca tttgaggtag ctgatccaat ccaattgatc      60
agtgtcaaaa ctgcactgtt cgtggaaatc atgcgcgttc tgcgcgatca gatttcgcag     120
caggcttcaa aggctgcatt gaagctcatt gtggagctct ttccgtgggg aagaaacagg     180
atcaaagggg ttgagggtgg tgctgttttg gtcctcgttg agttacttct tggtgcctcg     240
gaaagaagaa cgtgtgaact cattttgata gctttggatc agctttgtgg gtgtgcagaa     300
gggcgtgcag agttgttgaa ccatggagca ggagtggcca ttgtgtccaa gaaaattcta     360
agggtctctc atgtggcaag tgacagaggg gttagaattt tagcctctat ttgtaggtat     420
tccgccaatg ctagagtg                                                   438

<210> SEQ ID NO 8
<211> LENGTH: 264
<212> TYPE: PRT
<213> ORGANISM: Arabidopsis thaliana

<400> SEQUENCE: 8
```

Met Asp Gln Glu Ile Glu Ile Pro Ser Phe Phe Leu Cys Pro Ile Ser
1               5                   10                  15

Leu Asp Ile Met Lys Asp Pro Val Ile Val Ser Thr Gly Ile Thr Tyr
            20                  25                  30

Asp Arg Glu Ser Ile Glu Lys Trp Leu Phe Ser Gly Lys Lys Asn Ser
        35                  40                  45

Cys Pro Val Thr Lys Gln Val Ile Thr Glu Thr Asp Leu Thr Pro Asn
    50                  55                  60

His Thr Leu Arg Arg Leu Ile Gln Ser Trp Cys Thr Leu Asn Ala Ser
65                  70                  75                  80

Tyr Gly Ile Glu Arg Ile Pro Thr Pro Lys Pro Ile Cys Lys Ser
                85                  90                  95

Glu Ile Glu Lys Leu Ile Lys Glu Ser Ser Ser His Leu Asn Gln
                100                 105                 110

Val Lys Cys Leu Lys Arg Leu Arg Gln Ile Val Ser Glu Asn Thr Thr
            115                 120                 125

Asn Lys Arg Cys Leu Glu Ala Ala Glu Val Pro Glu Phe Leu Ala Asn
    130                 135                 140

Ile Val Ser Asn Ser Val Asp Thr Tyr Asn Ser Pro Ser Ser Ser Leu
145                 150                 155                 160

Ser Ser Ser Asn Leu Asn Asp Met Cys Gln Ser Asn Met Leu Glu Asn
                165                 170                 175

Arg Phe Asp Ser Ser Arg Ser Leu Met Asp Glu Ala Leu Ser Val Leu
                180                 185                 190

Tyr His Leu Asp Thr Ser Glu Thr Ala Leu Lys Ser Leu Leu Asn Asn
                195                 200                 205

Lys Lys Gly Thr Asn Leu Val Lys Thr Leu Thr Lys Ile Met Gln Arg
    210                 215                 220

Gly Ile Tyr Glu Ser Arg Ala Tyr Ala Ala Leu Leu Leu Lys Lys Leu
225                 230                 235                 240

Leu Glu Val Ala Asp Pro Met Gln Ile Ile Leu Leu Glu Arg Glu Leu
                245                 250                 255

Phe Gly Glu Val Ile Gln Ile Leu
                260

<210> SEQ ID NO 9
<211> LENGTH: 240
<212> TYPE: PRT
<213> ORGANISM: Arabidopsis thaliana

<400> SEQUENCE: 9

Met Ser Gly Gly Ile Met Asp Glu Glu Ile Glu Ile Pro Pro Phe Phe
1               5                   10                  15

Leu Cys Pro Ile Ser Leu Glu Ile Met Lys Asp Pro Val Ile Val Ser
            20                  25                  30

Thr Gly Ile Thr Tyr Asp Arg Asp Ser Ile Glu Lys Trp Leu Phe Ala
        35                  40                  45

Gly Lys Lys Asn Ser Cys Pro Val Thr Lys Gln Asp Ile Thr Asp Ala
    50                  55                  60

Asp Leu Thr Pro Asn His Thr Leu Arg Arg Leu Ile Gln Ser Trp Cys
65                  70                  75                  80

Thr Leu Asn Ala Ser Tyr Gly Val Glu Arg Ile Pro Thr Pro Arg Pro
                85                  90                  95

Pro Ile Cys Lys Ser Glu Ile Glu Lys Leu Ile Arg Asp Ser Ala Ser
                100                 105                 110

```
Ser His Glu Asn Gln Val Lys Cys Leu Lys Arg Leu Arg Gln Ile Val
    115                 120                 125
Ser Glu Asn Ala Thr Asn Lys Arg Cys Leu Glu Ala Ala Gly Val Pro
130                 135                 140
Glu Phe Leu Ala Asn Ile Val Ser Asn Asp Ser Glu Asn Gly Ser Leu
145                 150                 155                 160
Thr Asp Glu Ala Leu Asn Leu Leu Tyr His Leu Glu Thr Ser Glu Thr
                165                 170                 175
Val Leu Lys Asn Leu Leu Asn Asn Lys Lys Asp Asn Asn Ile Val Lys
            180                 185                 190
Ser Leu Thr Lys Ile Met Gln Arg Gly Met Tyr Glu Ser Arg Val Tyr
        195                 200                 205
Ala Thr Leu Leu Leu Lys Asn Ile Leu Glu Val Ala Asp Pro Met Gln
210                 215                 220
Ser Met Thr Leu Lys Pro Glu Val Phe Thr Glu Val Val Gln Ile Leu
225                 230                 235                 240

<210> SEQ ID NO 10
<211> LENGTH: 236
<212> TYPE: PRT
<213> ORGANISM: Glycine max

<400> SEQUENCE: 10

Met Asp Glu Ile Glu Ile Pro Ala His Phe Leu Cys Pro Ile Ser Leu
1               5                   10                  15
Gln Leu Met Arg Asp Pro Val Thr Val Cys Thr Gly Ile Thr Tyr Asp
            20                  25                  30
Arg Glu Asn Ile Glu Arg Trp Leu Phe Ser Cys Lys Asn Asn Thr Cys
        35                  40                  45
Pro Val Thr Lys Gln Cys Leu Leu Asn His Asp Leu Thr Pro Asn His
    50                  55                  60
Thr Leu Arg Arg Leu Ile Gln Ser Trp Cys Thr Leu Asn Ala Ser Leu
65                  70                  75                  80
Gly Val Glu Arg Ile Pro Thr Pro Lys Ser Pro Ile Asp Arg Thr Gln
                85                  90                  95
Ile Val Lys Leu Leu Thr Glu Ala Lys Arg Phe Pro Glu Lys Gln Leu
            100                 105                 110
Lys Cys Leu Thr Arg Leu Arg Ser Ile Ala Phe Glu Gly Gln Arg Asn
        115                 120                 125
Lys Thr Cys Leu Glu Ser Ala Gly Val Ile Glu Phe Leu Val Ser Thr
    130                 135                 140
Met Lys Asn Asn Thr Gln Glu Asp Ser Thr Val Leu Ser Glu Ala
145                 150                 155                 160
Ala Ile Glu Val Leu Phe His Leu Asn Leu Ser Glu Ala Arg Leu Lys
                165                 170                 175
Thr Leu Ile Asn Asn Glu Glu Phe His Phe Ile Glu Ser Leu Phe His
            180                 185                 190
Val Leu Arg Leu Gly Asn Tyr Gln Ser Arg Ala Phe Ala Thr Met Leu
        195                 200                 205
Leu Arg Ser Ala Phe Glu Val Ala Asp Pro Ile Gln Leu Ile Ser Val
    210                 215                 220
Lys Thr Ala Leu Phe Val Glu Ile Met Arg Val Leu
225                 230                 235

<210> SEQ ID NO 11
<211> LENGTH: 236
```

```
<212> TYPE: PRT
<213> ORGANISM: Glycine max

<400> SEQUENCE: 11

Met Asp Glu Ile Glu Ile Pro Ala His Phe Leu Cys Pro Ile Ser Leu
1               5                   10                  15

Gln Leu Met Arg Asp Pro Val Thr Val Cys Thr Gly Ile Thr Tyr Asp
            20                  25                  30

Arg Glu Asn Ile Glu Arg Trp Leu Phe Ser Cys Lys Asn Asn Thr Cys
        35                  40                  45

Pro Val Thr Lys Gln Cys Leu Leu Asp His Gly Leu Thr Pro Asn His
    50                  55                  60

Thr Leu Arg Arg Leu Ile Gln Ser Trp Cys Thr Leu Asn Ala Ser Leu
65                  70                  75                  80

Gly Val Glu Arg Ile Pro Thr Pro Lys Ser Pro Ile Asp Lys Thr Gln
                85                  90                  95

Ile Val Lys Leu Leu Thr Glu Ala Lys Arg Phe Pro Glu Lys Gln Leu
            100                 105                 110

Lys Cys Leu Thr Arg Leu Arg Ser Val Ala Phe Glu Gly Gln Arg Asn
        115                 120                 125

Lys Thr Cys Leu Glu Ser Ala Gly Val Ile Glu Phe Leu Ala Thr Thr
    130                 135                 140

Met Lys Asn Asn Asn Thr Gln Glu Asp Ser Thr Val Leu Ser Glu Ala
145                 150                 155                 160

Ala Ile Glu Val Leu Phe His Leu Asn Leu Ser Glu Ala Arg Leu Lys
                165                 170                 175

Thr Leu Ile Asn Asn Glu Glu Phe His Phe Ile Glu Ser Leu Phe His
            180                 185                 190

Val Leu Arg Leu Gly Asn Tyr Gln Ser Arg Val Tyr Ala Thr Met Leu
        195                 200                 205

Leu Arg Ser Ala Phe Glu Val Ala Asp Pro Ile Gln Leu Ile Ser Val
    210                 215                 220

Lys Thr Ala Leu Phe Val Glu Ile Met Arg Val Leu
225                 230                 235

<210> SEQ ID NO 12
<211> LENGTH: 244
<212> TYPE: PRT
<213> ORGANISM: Arabidopsis thaliana

<400> SEQUENCE: 12

Met Asp Gln Glu Glu Glu Ile Glu Ile Pro Asn Tyr Phe Ile Cys
1               5                   10                  15

Pro Ile Ser Leu Glu Ile Met Lys Asp Pro Val Thr Val Ser Gly
            20                  25                  30

Ile Thr Tyr Asp Arg Gln Asn Ile Val Lys Trp Leu Glu Lys Val Pro
        35                  40                  45

Ser Cys Pro Val Thr Lys Gln Pro Leu Pro Leu Asp Ser Asp Leu Thr
    50                  55                  60

Pro Asn His Met Leu Arg Arg Leu Ile Gln His Trp Cys Val Glu Asn
65                  70                  75                  80

Glu Thr Arg Gly Val Val Arg Ile Ser Thr Pro Arg Val Pro Pro Gly
                85                  90                  95

Lys Leu Asn Val Val Glu Glu Ile Lys Asn Leu Lys Lys Phe Gly Gln
            100                 105                 110

Glu Ala Leu Gly Arg Glu Glu Thr Leu Gln Lys Leu Glu Val Leu Ala
```

```
            115                 120                 125
Met Asp Gly Asn Asn Arg Arg Leu Met Cys Glu Cys Gly Val His Lys
130                 135                 140

Ser Leu Ile Leu Phe Val Val Lys Cys Thr Ser Glu Asp Glu Asp Gly
145                 150                 155                 160

Arg Arg Arg Ile Lys Gly Leu Asp Glu Ser Leu Arg Leu Leu His Leu
                165                 170                 175

Ile Gly Ile Pro Ser Asn Asp Ala Lys Thr Ile Leu Met Glu Asn Asp
            180                 185                 190

Arg Val Met Glu Ser Leu Thr Trp Val Leu His Gln Glu Asp Phe Leu
        195                 200                 205

Ser Lys Ala Tyr Thr Ile Val Leu Leu Arg Asn Leu Thr Glu Tyr Thr
    210                 215                 220

Ser Ser His Ile Val Glu Arg Leu Asn Pro Glu Ile Phe Lys Gly Ile
225                 230                 235                 240

Ile Gly Phe Leu

<210> SEQ ID NO 13
<211> LENGTH: 496
<212> TYPE: PRT
<213> ORGANISM: Oryza sativa

<400> SEQUENCE: 13

Met Ala Gly Asp Arg Ala Glu Glu Glu Gly Glu Ala Pro Pro Pro
1               5                   10                  15

Glu Ala Arg Ala Ala Ala Val Glu Arg Val Ala Ala Val Glu
                20                  25                  30

Ala Val Ala Ala Gly Ala Gly Ala Gly Glu Tyr Arg Asn Ala
            35                  40                  45

Tyr Arg Arg Gln Leu Leu Ala Leu Ser Arg Ile Arg Leu Leu Gly
    50                  55                  60

Pro Phe Val Glu Glu Leu Arg Glu Arg Arg Gly Glu Gly Glu Gly
65                  70                  75                  80

Glu Glu Glu Glu Arg Ala Leu Ala Pro Leu Ala Asp Ala Leu Glu Ala
                85                  90                  95

Ala Leu Ala Leu Leu Arg Leu Gly Arg Glu Gly Ser Arg Ile Ser Leu
            100                 105                 110

Val Leu Glu Arg Asp Ser Val Met Lys Lys Phe Gln Gly Val Ile Leu
        115                 120                 125

Gln Leu Glu Gln Ala Leu Cys Asp Ile Pro Tyr Asn Glu Leu Asp Ile
    130                 135                 140

Ser Asp Glu Val Arg Glu Gln Val Glu Leu Val His Ala Gln Leu Lys
145                 150                 155                 160

Arg Ala Lys Glu Arg Ile Asp Met Pro Asp Glu Phe Tyr Asn Asp
                165                 170                 175

Leu Leu Ser Val Tyr Asp Lys Asn Tyr Asp Pro Ser Ala Glu Leu Ala
            180                 185                 190

Ile Leu Gly Arg Leu Ser Glu Lys Leu His Leu Met Thr Ile Thr Asp
        195                 200                 205

Leu Thr Gln Glu Ser Leu Ala Leu His Glu Met Val Ala Ser Gly Gly
    210                 215                 220

Gly Gln Asp Pro Gly Glu His Ile Glu Arg Met Ser Met Leu Leu Lys
225                 230                 235                 240

Lys Ile Lys Asp Phe Val Gln Thr Gln Asn Pro Asp Met Gly Pro Pro
                245                 250                 255
```

```
Met Ala Ser Arg Val Leu Asp Ser Asn Gly Asp Ser Arg Pro Ile Thr
            260                 265                 270

Ile Pro Asp Glu Phe Arg Cys Pro Ile Ser Leu Glu Leu Met Lys Asp
        275                 280                 285

Pro Val Ile Val Ser Thr Gly Ala Cys Ile Glu Lys Trp Ile Ala Ser
        290                 295                 300

Gly His His Thr Cys Pro Thr Thr Gln Gln Lys Met Ser Thr Ser Ala
305                 310                 315                 320

Leu Thr Pro Asn Tyr Val Leu Arg Ser Leu Ile Ser Gln Trp Cys Glu
                325                 330                 335

Thr Asn Gly Met Glu Pro Pro Lys Arg Ser Thr Gln Pro Asn Lys Pro
            340                 345                 350

Thr Pro Ala Cys Ser Ser Ser Glu Arg Ala Asn Ile Asp Ala Leu Leu
        355                 360                 365

Ser Lys Leu Cys Ser Pro Asp Thr Glu Glu Gln Arg Ser Ala Ala Ala
        370                 375                 380

Glu Leu Arg Leu Leu Ala Lys Arg Asn Ala Asn Asn Arg Ile Cys Ile
385                 390                 395                 400

Ala Glu Ala Gly Ala Ile Pro Leu Leu Leu Ser Leu Leu Ser Ser Ser
                405                 410                 415

Asp Leu Arg Thr Gln Glu His Ala Val Thr Ala Leu Leu Asn Leu Ser
            420                 425                 430

Ile His Glu Asp Asn Lys Ala Ser Ile Ile Ser Ser Gly Ala Val Pro
        435                 440                 445

Ser Ile Val His Val Leu Lys Asn Gly Ser Met Glu Ala Arg Glu Asn
        450                 455                 460

Ala Ala Ala Thr Leu Phe Ser Leu Ser Val Ile Asp Glu Tyr Lys Val
465                 470                 475                 480

Thr Ile Gly Gly Met Gly Ala Ile Pro Ala Leu Val Val Leu Leu Gly
                485                 490                 495

<210> SEQ ID NO 14
<211> LENGTH: 24
<212> TYPE: DNA
<213> ORGANISM: Artificial Sequence
<220> FEATURE:
<223> OTHER INFORMATION: description of artificial sequence: sequencing
      primer named pB42ADF used to identify positive Ubox clones

<400> SEQUENCE: 14
ccagcctctt gctgagtgga gatg                                            24

<210> SEQ ID NO 15
<211> LENGTH: 22
<212> TYPE: DNA
<213> ORGANISM: Artificial Sequence
<220> FEATURE:
<223> OTHER INFORMATION: description of artificial sequence: sequencing
      primer named pB42ADR used to identify positive Ubox clones

<400> SEQUENCE: 15
caaggtagac aagccgacaa cc                                              22

<210> SEQ ID NO 16
<211> LENGTH: 31
<212> TYPE: DNA
<213> ORGANISM: Artificial Sequence
<220> FEATURE:
<223> OTHER INFORMATION: description of artificial sequence: forward
      primer used to amplify Avr1b sequence
```

```
<400> SEQUENCE: 16
gactaagctt cgatgcgtct atcttttgtg c                                      31

<210> SEQ ID NO 17
<211> LENGTH: 31
<212> TYPE: DNA
<213> ORGANISM: Artificial Sequence
<220> FEATURE:
<223> OTHER INFORMATION: description of artificial sequence:  reverse
      primer used to amplify Avr1b sequence

<400> SEQUENCE: 17
agtcggatcc tcactggtgg tgctggtggt g                                      31

<210> SEQ ID NO 18
<211> LENGTH: 33
<212> TYPE: DNA
<213> ORGANISM: Artificial Sequence
<220> FEATURE:
<223> OTHER INFORMATION: description of artificial sequence:  forward
      primer used to amplify Ubox core sequence

<400> SEQUENCE: 18
gactagatct cgatgcaatc ttggtgcacc ctc                                    33

<210> SEQ ID NO 19
<211> LENGTH: 32
<212> TYPE: DNA
<213> ORGANISM: Artificial Sequence
<220> FEATURE:
<223> OTHER INFORMATION: description of artificial sequence:  reverse
      primer used to amplify Ubox core sequence

<400> SEQUENCE: 19
caggatcccg ggttcctttg ccctctcctt ag                                     32
```

COMPOSITIONS AND METHODS FOR ENHANCING DISEASE RESISTANCE IN PLANTS

CROSS-REFERENCE TO RELATED APPLICATIONS

This application claims priority under 35 U.S.C. §119 of a provisional application Ser. No. 61/110,510 filed Oct. 31, 2008, which application is hereby incorporated by reference in its entirety.

BACKGROUND OF THE INVENTION

Soybean is a major oil seed crop and is grown throughout much of the world. The United States alone produces over half of the world output. Soybean seed typically contains 40% protein and 20% oil and is used primarily for livestock feed and industrial purposes, in addition to human consumption. In North America, soybean suffers yield loss from the root and stem rot disease caused by oomycete pathogen *Phytophthora sojae*. In the United States the annual crop losses from this disease were valued to about 0.2 to 0.3 billion dollars (Wrather et al. 2001). Plant resistance to this and other sort of pathogens present a major problem to soybean growers. For these and other reasons, there is a need to enhance resistance to diseases caused by pathogens in plants without harming the transgenic plant and without resorting to use of environmentally damaging chemicals.

SUMMARY

In one aspect, this invention relates to GmUBox1 sequences (*Glycine max* U-Box) isolated from soybean (*Glycine max*) which when expression is eliminated or decreased may increase disease resistance to an oomycete pathogen such as *Phytophthora*. Also according to the invention, protein sequences are disclosed which are encoded by these sequences. This sequence alone, or in combination with other sequences, can be used to improve the soybean resistance to pathogens such as an oomycete pathogen such as *Phytophthora*. In another aspect of the present invention, expression cassettes and transformation vectors comprising the isolated nucleotide sequences are disclosed. The transformation vectors can be used to transform plants and express these pathogen control genes in the transformed cells. Transformed cells as well as regenerated transgenic plants and seeds containing and expressing the isolated DNA sequences and protein products are also provided.

Therefore, in one aspect, the present invention relates to an isolated nucleic acid comprising an isolated polynucleotide sequence encoding a GmUBox gene product. In a further aspect, the present invention includes a nucleic acid selected from: (a) an isolated polynucleotide encoding a polypeptide of the present invention; (b) a polynucleotide having at least 70% identity to a polynucleotide of the present invention; (c) a polynucleotide comprising at least 50 or more nucleotides in length which hybridizes under high stringency conditions to a polynucleotide of the present invention; (d) a polynucleotide comprising a polynucleotide of the present invention; and (e) a polynucleotide which is complementary to the polynucleotide of (a) to (e).

In another aspect, the present invention relates to a recombinant expression cassette comprising a nucleic acid as described, supra. Additionally, the present invention relates to a vector containing the recombinant expression cassette. Further, the vector containing the recombinant expression cassette can facilitate the transcription and/or translation of the nucleic acid in a host cell. Preferably the polynucleotide is in antisense orientation. The present invention also relates to host cells able to express the polynucleotide of the present invention. A number of host cells could be used, such as but not limited to, microbial, mammalian, plant, or insect. Thus the invention is also directed to transgenic cells, containing the nucleic acids of the present invention as well as cells, plants, tissue cultures and ultimately lines derived therefrom. The invention also relates to vectors and cassettes designed to down regulate or inhibit the expression of a GmUBox1 protein of the invention for modulating disease resistance associated with a pathogen or for modulating tolerance to an environmental stress.

This invention also provides an isolated polypeptide comprising (a) a polypeptide comprising at least 70% sequence identity to a polypeptide of the present invention (b) a polypeptide encoded by a nucleic acid of the present invention; (c) a polypeptide comprising GmUBox1 activity, and (d) a polypeptide that functions as a dominant negative mutant of GmUBox1.

Another embodiment of the subject invention comprises a method for engineering broad spectrum pathogen resistance in plants by modulating the GmUBox1 proteins, for example, in soybean plants. Plants' tolerance to oomycete pathogens such as *Phytophthora* and other soybean pathogens may be improved by eliminating or decreasing GmUBox1 expression or activity.

Plants that have decreased GmUBox1 expression or activity, for example, created using the methods described herein, may be used in breeding programs for incorporating *Phytophthora* resistance or broad spectrum pathogen resistance into new soybean cultivars.

FIGURES

FIG. 1: Sequences of two GmUBox1 genes of GmUBox1-1 and GmUBox1-2. The two genes show 94% amino acid identity. A) cDNA for GmUBox1-1, B) cDNA for GmUBox1-2, C) alignment of amino acid sequences of GmUBox1-1 and GmUBox1-2, D) amino acid sequence for GmUBox1-1, E) amino acid sequence for GmUBox1-2.

FIG. 2: Sequence comparison of two genomic regions carrying GmUBox1 genes show conservation of gene orders as shown by high identities through out most of the 70 kb region containing the GmUBox1 genes at the center (shown with a black box). Gap regions show lack of identities because of absence of pairs of coding sequences or noncoding intergenic regions.

FIG. 3: Sequence comparison of GmUBox1 proteins with homologous *Arabidopsis* PUB and rice SPL11 proteins. *, showed the conserved residues of the U-box domain.

Figure 4:
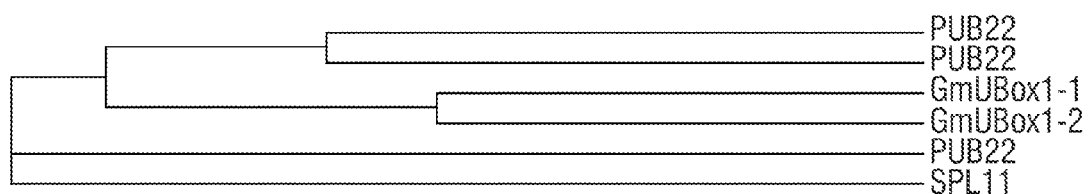

FIG. 4: Phylogenetic tree of the GmUBox1-like sequences. GmUBox1 is closest to *Arabidopsis* PUB23.

Figure 5:
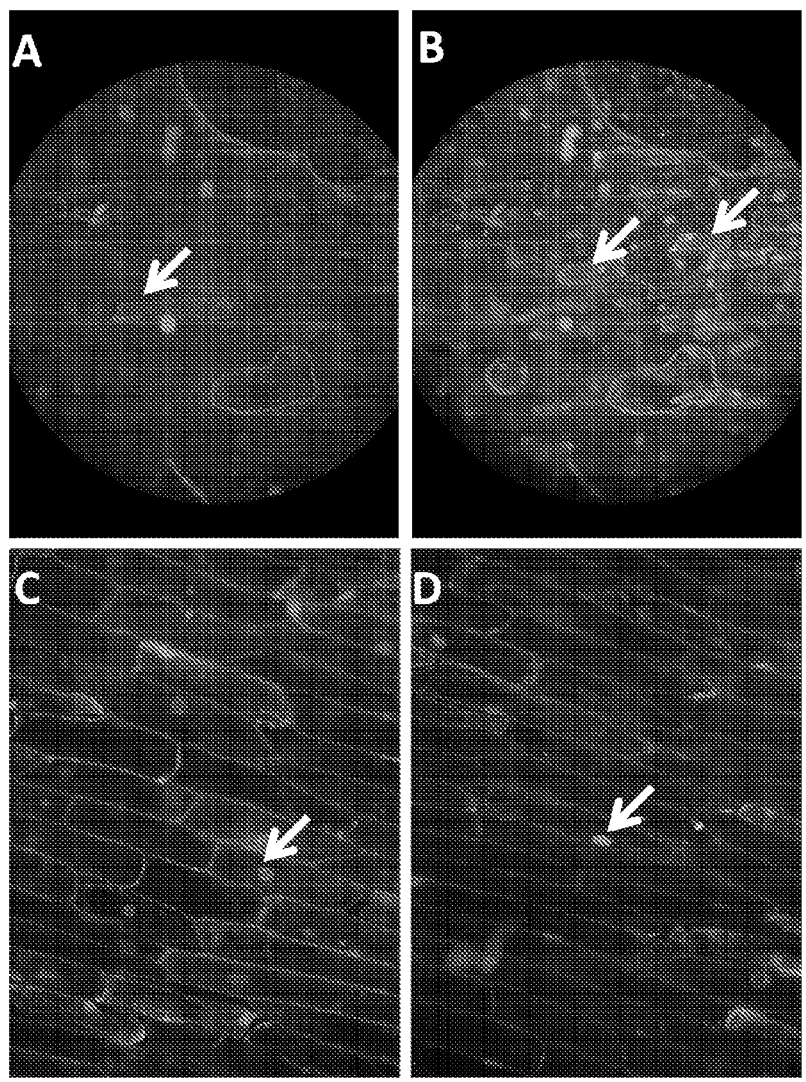

FIG. 5: BiFC Analysis showed in planta (onion cells) interaction between U-box Protein and Avr1b. A) RFP control show successful transient expression (arrow shows the cell expressing RFP); B) the same area shown in A) shows cells with BiFC; C) BiFC is observed in nuclei and cytoplasm. This may suggest that the protein-protein interaction takes place inside nuclei (arrows). Fluorescence (shown by arrows in B, C, D) observed from complementation of the C-terminal part of the YFP fused with Avr1b (Avr1b-C-EYFP) with the N-terminal part of the YFP fused with U-box (U-box-N-EYFP) indicates in planta interaction between the two proteins.

Figure 6:
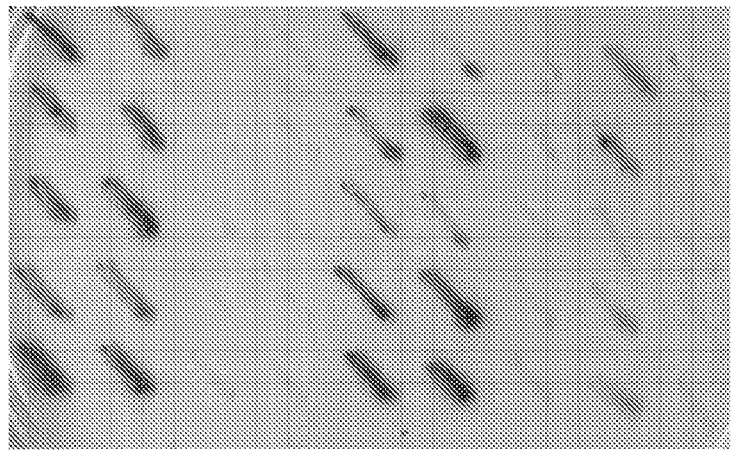

FIG. 6: GmUBox1-1 interacts with Avr1b mutants W1, W2, W5, W6 and Avr1b. Avr1b mutants, W3, W4 and Y1 showed loss of interaction with U-box. The isoleucine of W motif (W2), mutated in W3 and W4, is conserved across most paralogous Avr1b proteins.

FIG. 7 shows polynucleotide (A) and translated protein (B) sequences of GmUBox1 from Yeast two hybrid interacting clones. (GmUBox1-1 dominant negative)

FIG. 8 Exemplary sequence for generating RNAi molecules (SEQ ID NO.:7). RNAi fragments may be selected for similarity or identity with the second half of the GmUBox1 sequences.

DETAILED DESCRIPTION OF THE PREFERRED EMBODIMENT

Definitions

For clarity, certain terms used in the specification are defined and presented as follows:

It is to be understood that as used in the specification and in the claims, "a" or "an" can mean one or more, depending upon the context in which it is used.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric construct" is a recombinant nucleic acid sequence in which a promoter or regulatory nucleic acid sequence is operatively linked to, or associated with, a nucleic acid sequence that codes for an mRNA or which is expressed as a protein, such that the regulatory nucleic acid sequence is able to regulate transcription or expression of the associated nucleic acid sequence. The regulatory nucleic acid sequence of the chimeric construct is not normally operatively linked to the associated nucleic acid sequence as found in nature.

Co-factor: natural reactant, such as an organic molecule or a metal ion, required in an enzyme-catalyzed reaction. A co-factor is e.g. NAD(P), riboflavin (including FAD and FMN), folate, molybdopterin, thiamin, biotin, lipoic acid, pantothenic acid and coenzyme A, S-adenosylmethionine, pyridoxal phosphate, ubiquinone, menaquinone. Optionally, a co-factor can be regenerated and reused.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

Complementary: "complementary" refers to two nucleotide sequences that comprise antiparallel nucleotide sequences capable of pairing with one another upon formation of hydrogen bonds between the complementary base residues in the antiparallel nucleotide sequences.

Enzyme activity: means herein the ability of an enzyme to catalyze the conversion of a substrate into a product. A substrate for the enzyme comprises the natural substrate of the enzyme but also comprises analogues of the natural substrate, which can also be converted, by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

As used herein, "expression" refers to the process by which a polypeptide is produced based on the nucleic acid sequence of a gene. The process includes both transcription and translation.

Expression Cassette: "Expression cassette" as used herein means a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue or organ or stage of development.

Gene: the term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

Heterologous/exogenous: The terms "heterologous" and "exogenous" when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

"Endogenous" with reference to a polynucleotide or protein refers to a polynucleotide or protein that occurs naturally in the host cell.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, or temperature, or combinations thereof, and in particular, can be high salinity, low water content or low temperature.

A "homologous" nucleic acid (e.g. DNA) sequence is a nucleic acid (e.g. DNA) sequence naturally associated with a host cell into which it is introduced.

Hybridization: The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

Inhibitor: a chemical substance that inactivates the enzymatic activity of a protein such as a biosynthetic enzyme, receptor, signal transduction protein, structural gene product, or transport protein. The term "herbicide" (or "herbicidal compound") is used herein to define an inhibitor applied to a plant at any stage of development, whereby the herbicide inhibits the growth of the plant or kills the plant.

Interaction: quality or state of mutual action such that the effectiveness or toxicity of one protein or compound on another protein is inhibitory (antagonists) or enhancing (agonists).

A nucleic acid sequence is "isocoding with" a reference nucleic acid sequence when the nucleic acid sequence encodes a polypeptide having the same amino acid sequence as the polypeptide encoded by the reference nucleic acid sequence.

Isogenic: plants that are genetically identical, except that they may differ by the presence or absence of a heterologous DNA sequence.

Isolated: in the context of the present invention, an isolated DNA molecule or an isolated enzyme is a DNA molecule or enzyme that, by the hand of man, exists apart from its native environment and is therefore not a product of nature. An isolated DNA molecule or enzyme may exist in a purified form or may exist in a non-native environment such as, for example, in a transgenic host cell.

Mature protein: protein from which the transit peptide, signal peptide, and/or propeptide portions have been removed.

Minimal Promoter: the smallest piece of a promoter, such as a TATA element, that can support any transcription. A minimal promoter typically has greatly reduced promoter activity in the absence of upstream activation. In the presence of a suitable transcription factor, the minimal promoter functions to permit transcription.

Modified Enzyme Activity: enzyme activity different from that which naturally occurs in a plant (i.e. enzyme activity that occurs naturally in the absence of direct or indirect manipulation of such activity by man), which is tolerant to inhibitors that inhibit the naturally occurring enzyme activity.

Native: refers to a gene that is present in the genome of an untransformed plant cell.

Naturally occurring: the term "naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

Nucleic acid: the term "nucleic acid" and "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. For example, antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). The terms "nucleic acid" or "nucleic acid sequence" may also be used interchangeably with gene, cDNA, and mRNA encoded by a gene. "ORF" means open reading frame.

As also used herein, the term "nucleic acid" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

"Operably-linked" refers to juxtaposition wherein elements are in an arrangement allowing them to be functionally related, even where not in close physical proximity. For example, a promoter is operably-linked to a coding sequence if it is capable of controlling the coding sequence and does control the transcription of the sequence under conditions permissive thereof, or conducive thereto.

As used herein, "optimized" in reference to nucleic acid expression refers to a nucleic acid that is genetically engineered to increase its expression in a given plant or animal. To provide plant optimized GmUBox1 nucleic acids, the DNA sequence of the gene can be modified to 1) comprise codons preferred by highly expressed plant genes; 2) comprise an A+T content in nucleotide base composition to that substantially found in plants; 3) form a plant initiation sequence, 4) to eliminate sequences that cause destabilization, inappropriate polyadenylation, degradation and termination of RNA, or that form secondary structure hairpins or RNA splice sites. Increased expression of GmUBox1 nucleic acids in plants can be achieved by utilizing the distribution frequency of codon usage in plants in general or a particular plant. Methods for optimizing nucleic acid expression in plants can be found in EPA 0359472; EPA 0385962; WO 91/16432; U.S. Pat. No. 5,380,831; U.S. Pat. No. 5,436,391; Perlack et al. (1991) Proc. Natl. Acad. Sci. USA 88:3324 3328; and Murray et al. (1989) Nucleic Acids Res. 17:477 498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A=n=1ZX_n-Y_nX_n$ times 100 Z where $X_n$=frequency of usage for codon n in the host cell; $Y_n$=frequency of usage for codon n in the synthetic gene, n represents an individual codon that specifies an amino acid and the total number of codons is Z. The overall deviation of the frequency of codon usage, A, for all amino acids should preferably be less than about 25%, and more preferably less than about 10%.

The term "plant" includes whole plants, plant parts (e.g., leaves, stems, flowers, roots, etc.), plant protoplasts, seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous states.

Percent identity: the phrases "percent identical" or "percent identical," in the context of two nucleic acid or protein sequences, refers to two or more sequences or subsequences that have for example at least 60%, 70%, 80%, 90%, 90%, 91%, 92%, 93%, 94%, 95%, 96%, 97%, 98%, or 99% nucleotide or amino acid residue identity, when compared and aligned for maximum correspondence, as measured using one of the following sequence comparison algorithms or by visual inspection. Preferably, the percent identity exists over a region of the sequences that is at least about 50 residues in length, more preferably over a region of at least about 100 residues, and most preferably the percent identity exists over at least about 150 residues. In an especially preferred embodiment, the percent identity exists over the entire length of the coding regions.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (http://www.ncbi.nim.nih.go-v/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Pre-protein: protein that is normally targeted to a cellular organelle, such as a chloroplast, and still comprises its native transit peptide.

The terms "protein" and "polypeptide" are used interchangeably herein. The conventional one-letter or three-letter code for amino acid residues is used herein.

As used herein, the term "promoter" includes all sequences capable of driving transcription of a polynucleotide sequence in a cell, e.g., a plant cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

Purified: the term "purified," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination.

"Regulatory elements" refer to sequences involved in controlling the expression of a nucleotide sequence. Regulatory elements comprise a promoter operatively linked to the nucleotide sequence of interest and termination signals. They also typically encompass sequences required for proper translation of the nucleotide sequence.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

Significantly less: means that the amount of a product of an enzymatic reaction is reduced by more than the margin of error inherent in the measurement technique, preferably a decrease by about 2-fold or greater of the activity of the wild-type enzyme in the absence of the inhibitor, more preferably an decrease by about 5-fold or greater, and most preferably an decrease by about 10-fold or greater.

Specific Binding/Immunological Cross-Reactivity: An indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions. The phrase "specifically (or selectively) binds to an antibody," or "specifically (or selectively) immunoreactive with," when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the protein with the amino acid sequence encoded by any of the nucleic acid sequences of the invention can be selected to obtain antibodies specifically immunoreactive with that protein and not with other proteins except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) Antibodies, A Laboratory Manual, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or Northern blot is 50% formamide with 1 mg of heparin at 42°

C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone nucleotide sequences that are homologues of reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

A "subsequence" refers to a sequence of nucleic acids or amino acids that comprise a part of a longer sequence of nucleic acids or amino acids (e.g., protein) respectively.

The phrase "substantially identical" in the context of two nucleic acids or polypeptides, refers to two or more sequences that have, e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more nucleotide or amino acid residue (sequence) identity, when compared and aligned for maximum correspondence, as measured using one of the known sequence comparison algorithms or by visual inspection. Typically, the substantial identity exists over a region of at least about 100 residues and most commonly the sequences are substantially identical over at least about 150-200 residues. In some aspects, the sequences are substantially identical over the entire length of the coding regions. Thus, one embodiment of the invention is a polynucleotide molecule that has at least about 70%, 75%, 80%, 85%, 90%, 91%, 92%, 93%, 94%, 95%, 96%, 97%, 98%, or 99% sequence identity with a polynucleotide sequence described herein, for example, that of SEQ ID NO:1, 2, 5 or 7. Another embodiment of the invention is a polypeptide molecule that has at least about 70%, 75%, 80%, 85%, 90%, 91%, 92%, 93%, 94%, 95%, 96%, 97%, 98%, or 99% sequence identity with a polypeptide sequence described herein, for example, that of SEQ ID NO:3, 4 or 6.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a GmUBox1 polypeptide, resulting in modification of the structure of the polypeptide, for example, to make a dominant negative. Modified polypeptide sequences of the invention can be assayed for GmUBox1 activity by any number of methods. See, for example, Examples 7 and 12.

Substrate: a substrate is the molecule that an enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Transformation: a process for introducing heterologous DNA into a plant cell, plant tissue, or plant. Transformed plant cells, plant tissue, or plants are understood to encompass not only the end product of a transformation process, but also transgenic progeny thereof.

"Transformed," "transgenic," and "recombinant" refer to a host organism such as a yeast, bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a yeast, bacterium or plant, which does not contain the heterologous nucleic acid molecule.

As used herein, the term "transgenic plant" includes plants or plant cells into which a heterologous nucleic acid sequence has been inserted, e.g., the nucleic acids and various recombinant constructs (e.g., expression cassettes) of the invention.

As used herein, the term "variant" may be used interchangeably with the term "mutant." "Variants" can refer to either polypeptides or nucleic acids. Variants include one or more sequence "modifications," which as used herein include substitutions, insertions, deletions, truncations, transversions, and/or inversions, at one or more locations relative to a reference sequence. Each modification can include changes that result in a change of one or more amino acid residues or nucleotides in a sequence, relative to the reference sequence.

Viability: "viability" as used herein refers to a fitness parameter of a plant. Plants are assayed for their homozygous performance of plant development, indicating which proteins are essential for plant growth.

I. Introduction

The present invention now will be described more fully hereinafter with reference to the accompanying examples, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the invention set forth herein will come to mind to one skilled in the art to which this invention pertains, having the benefit of the teachings presented in the descriptions and the drawings herein. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The ubiquitin/proteasome pathway is a major mechanism of protein degradation in eukaryotes. In this pathway, a target protein is tagged by the covalent attachment of ubiquitin molecules before degradation by the 26S proteasome complex composed of several proteins. Three main enzymes catalyze a series of ubiquitination reactions. First ubiquitin is activated by an ubiquitin-activating enzyme (E1) and then transferred to the active site of E2 ubiquitin-conjugating enzyme. An ubiquitin ligase (E3) then binds E2 and catalyzes the formation of an isopeptide linkage between the activated ubiquitin and the substrate protein. In plants, ubiquitination-mediated protein degradation has been shown to play a significant role in multiple cellular processes, such as photomorphogenesis and hormone signaling, and disease resistance.

Ubiquitin ligases (E3) have generally been separated into two groups, those containing HECT domains and those with RING finger domains. Recently, a third group containing a U-box domain has been identified. The U-box proteins are predicted to be either E3 or E4 factors in the ubiquitination pathway. There are much more U-box proteins in plants than in other organisms. A database search revealed 37 predicted proteins containing U-box domains in *Arabidopsis* classified into five distinct subclasses (Azevedo C., Santos-Rosa M. J. Shirasu K. (2001) The U-box protein family in plants. Trends in Plant Science 6:8). These *Arabidopsis* U-box proteins are named PUBs. The U-box motif of ~70 amino acids is highly conserved among the PUB proteins.

Plant U-box proteins are implicated in self-incompatibility (Stone, S. L., Anderson, E. M., Mullen, R. T., and Goring, D. R. (2003) ARC1 is an E3 ubiquitin ligase and promotes the ubiquitination of proteins during the rejection of self-incompatible *Brassica* pollen. Plant Cell 15:885-898), responses to hormones (Amador, V., Monte, E., García-Martínez, J. L., and Prat, S. (2001) Gibberellins signal nuclear import of PHOR1, a photoperiod-responsive protein with homology to *Drosophila* armadillo. Cell 106: 343-354), abiotic stress (Yan et al. 2003), and hormone regulation (Amador, V., Monte, E., García-Martínez, J. L., and Prat, S. (2001) Gibberellins signal nuclear import of PHOR1, a photoperiod-responsive protein with homology to *Drosophila* armadillo. Cell 106: 343-354). Cho S. K., Ryu M. Y., Song C., Kwak J. M., Kima W. T. (2008) *Arabidopsis* PUB22 and PUB23 Are Homologous U-Box E3 Ubiquitin Ligases That Play Combinatory Roles in Response to Drought Stress. Plant Cell Preview. www.aspb.org) showed *Arabidopsis* PUB22 and PUB23 are homologous U-Box E3 ubiquitin ligases that function as negative regulators of the water stress responses.

U-Box proteins may play an important role in plant defense against pathogens. *Capsicum annuum* L. cv Pukang (Hot pepper) CaPUB1 also encodes a U-Box E3 ubiquitin ligase, which is involved in the early events of defense responses (Cho S. K., Chung H. S., Ryu M. Y., Park M. J., Lee M. M., Bahk Y. Y., Kim J., Pai H. S., Kim W. T. (2006) Heterologous Expression and Molecular and Cellular Characterization of CaPUB1 Encoding a Hot Pepper U-Box E3 Ubiquitin Ligase Homolog. Plant Physiology 142:1664-1682). Yang et al. Yang, C., Lamothe. R. G., Ewan, R. A., Rowland, O., Yoshioka, H., Shenton, M., Ye, H., Donnell, E., Jones, J. D., and Sadanandom, A. (2006) The E3 Ubiquitin Ligase Activity of *Arabidopsis* PLANT U-BOX17 and Its Functional Tobacco Homolog ACRE276 Are Required for Cell Death and Defense. Plant Cell 18: 1084-1098) identified several Avr9/Cf-9 rapidly elicited (ACRE) genes, which were required for full Cf-mediated defenses. One of them, ACRE276 encodes a U-box protein with ARMADILLO (ARM) repeat domains. The E3 ubiquitin ligase activity of ACRE276 and its functional homolog *Arabidopsis* PUB17 is essential for cell death and defense. Another U-box protein, tobacco CMPG1 with high homology to parsley (*Petroselinum crispum*) CMPG1 and *Arabidopsis thaliana* PUB20 and PUB21 proteins (Lamothe, R. G., Tsitsigiannis, D. I., Ludwig, A. A., Panicot M., Shirasu K., and Jones, J. D. (2006) The U-Box Protein CMPG1 Is Required for Efficient Activation of Defense Mechanisms Triggered by Multiple Resistance Genes in Tobacco and Tomato. The Plant Cell 18:1067-1083) induced in Cf9 containing transgenic tobacco after elicitation with Avr9 and required for activation of defense mechanisms triggered by resistance genes.

U-box proteins may also function as a negative regulator of cell death and defense against pathogens. Zeng, L., Qu, S., Bordeos, A., Yang, C., Baraoidan, M., Yan, H., Xie, Q., Nahm, B. H., Leung, H., Wang, G. (2004) Spotted leaf11, a Negative Regulator of Plant Cell Death and Defense, Encodes a U-Box/Armadillo Repeat Protein Endowed with E3 Ubiquitin Ligase Activity. Plant Cell 16:2795-2808) identified the Spl11 gene encoding a novel protein with both a U-box domain and six armadillo (ARM) repeats, mutation of which caused lesion mimic mutation, spotted leaf11 (spl11). The ethyl methane sulfonate-induced rice mutation, spl11 displayed spontaneous lesions and enhanced resistance to both *Magnaporthe grisea* and *Xanthomonas oryzae* pv *oryzae*. Expression pattern of Spl11 in infected rice plants with the blast fungus, *M. grisea* suggested that Spl11 is not R gene dependent and might be involved in the basal defense signaling against the rice blast pathogen. Recently Trujillo et al. (Trujillo M., Ichimura K., Casais C., and Shirasu K. (2008) Negative Regulation of PAMP-Triggered Immunity by an E3 Ubiquitin Ligase Triplet in *Arabidopsis*. Current Biology 18:1396-1401) have showed that three homologous U-box type E3 ubiquitin ligases, PUB22, PUB23, and PUB24 act as negative regulators of pathogen-associated molecular patterns (PAMPs) triggered immunity (PTI) in *Arabidopsis*. The pub22/pub23/pub24 triple mutant displayed increased PTI responses and enhanced resistance against bacterial and oomycete pathogens.

An important strategy used by bacterial pathogens in causing disease is mimicking eukaryotic biochemical processes to suppress the host defense responses. Many bacterial pathogens of plants use a type III secretion system to deliver diverse virulence-associated 'effector' proteins into the host cell. They often promote disease by suppressing host immunity. A bacterial pathogen effector protein in fact carries an E3 ligase domain that promotes disease symptoms by inhibiting host programmed cell death required for defenses (Janjusevic, R., Abramovitch R., Martin G., Stebbins C. E. (2006) A Bacterial Inhibitor of Host Programmed Cell Death Defenses Is an E3 Ubiquitin Ligase. Science 311: 222).

The sequences of the invention are based, in part, on the discovery of two GmUBox1 polynucleotides isolated from soybean. The present invention provides novel isolated polynucleotides encoding GmUBox1 proteins cloned through their interaction with the oomycete avirulence protein (similar to bacterial effector proteins), Avr1b. As shown in FIG. 5, the GmUBox1-1 protein interacts with the *Phytophthora sojae* Avr1b protein in yeast and onion cells. FIG. 4 shows that GmUBox1 proteins are highly similar to *Arabidopsis* PUB22, PUB23 and PUB24 and rice Spl11 proteins.

As used herein, the term GmUBox1 includes but is not limited to the sequences disclosed herein, such as GmUBox1-1 and GmUBox1-2, their fragments, dominant negatives, conservatively modified variants, regardless of source and any other variants which retain the biological properties of the GmUBox1, for example, GmUBox1 activity as disclosed herein.

The present invention provides polynucleotides encoding GmUBox1 sequences, transgenic plants comprising the polynucleotides and methods for modulating disease resistance associated with pathogens or ubiquitination-mediated protein degradation in plants. Methods to produce a plant with enhanced disease resistance to a pathogen in the plant includes disrupting one or more genes encoding GmUBox1 proteins, decreasing the expression of one or more GmUBox1 proteins, or decreasing the activity of one or more GmUBox1 proteins or combinations thereof.

In one embodiment, the present invention includes methods of creating disease resistant plants using compositions of the present invention in conjunction with antisense, siRNA, RNAi, co-suppression, knock out techniques, dominant negatives, or any other techniques to genetically engineer the loss, or partial loss, of expression and/or activity of GmUBox1 sequences in a plant cell, preferably soybean.

The invention also provides gene constructs that disrupt or decrease the expression and/or activity of GmUBox1 proteins in a cell, for example, a plant cell. Accordingly, the invention provides novel compositions and methods for increasing or decreasing the level and/or activity of one or more GmUBox1 polynucleotides or polypeptides of the present invention in a plant cell or plant. The result of disrupting or decreasing the expression or activity of the GmUBox1 proteins may be enhanced resistance to a disease caused by a pathogen in the plant.

As used herein, "enhanced or enhancing disease resistance to a pathogen", refers to an increase and/or improved resistance to disease caused by a pathogen compared to the resistance to disease caused by a pathogen in a control plant. For example, enhanced disease resistance of a plant to a particular disease or pathogen, for example, may be assessed by comparing symptoms of the pathogen in a transgenic plant and non-transgenic control plant, for example, the symptoms associated with the pathogenic disease, for example, hallmarks of the disease such as certain physical features and characteristics. This also includes a level of endurance to a pathogen in a transgenic plant which is greater than that exhibited by a control plant (for example, a non-transgenic plant). By disease resistance is intended that the plants avoid or have ameliorated disease symptoms which are the outcome of plant-pathogen interactions.

The methods of the invention can be utilized to protect plants from disease, particularly those diseases that are caused by plant pathogens in soybeans. In this manner, resistance to these fungal pathogens and other pathogens such as *Phytophthora sojae, Pseudomonas syringae* pv. *glycinea* (Psg), soybean cyst nematode (SCN), or soybean mosaic virus (SMV) can be enhanced or improved in the transformed plant or its progeny when using the sequences and methods of the present invention.

The methods of the invention can be utilized to protect plants from disease, particularly those diseases that are caused by plant pathogens, such as oomycete pathogens, in soybeans. In this manner, resistance to these fungal pathogens and other pathogens such as *Phytophthora sojae, Pseudomonas syringae* pv. *glycinea* (Psg), soybean cyst nematode (SCN), or soybean mosaic virus (SMV) can be enhanced or improved in the transformed plant or its progeny when using the sequences and methods of the present invention. The invention further provides transgenic plant parts and transgenic plants containing the plant cells described herein. The transgenic plants have enhanced resistance to a disease or disease-induced by pathogen, such as an oomycete pathogen, or broad spectrum pathogen resistance. Also provided is a plant seed produced by the transgenic plant.

II. Isolation of Nucleic Acids of the Invention

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In some embodiments, an "isolated" nucleic acid is free of sequences (such as other protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, 0.4 kb, 0.3 kb, 0.2 kb, or 0.1 kb, or 50, 40, 30, 20, or 10 nucleotides that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, culture medium may represent less than about 30%, 20%, 10%, or 5% (by dry weight) of chemical precursors or non-protein-of-interest chemicals.

Fragments and variants of the disclosed nucleotide sequences are encompassed by the present invention. Fragments and variants of proteins encoded by the disclosed nucleotide sequences are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence affect development, developmental pathways, stress responses, and/or disease resistance by retaining GmUBox1 activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a GmUBox1 nucleotide sequence that encodes a biologically active portion of a GmUBox1 protein of the invention will encode at least 12, 25, 30, 50, 75, 100, 150, 200, 250, 300, 350, 400 etc. contiguous amino acids, or up to the total number of amino acids present in a full-length GmUBox1 protein of the invention.

Fragments of a GmUBox1 nucleotide sequence that are useful as hybridization probes or PCR primers generally may or may not encode a biologically active portion of a protein. Thus, a fragment of a GmUBox1 nucleotide sequence may encode a biologically active portion of a GmUBox1 protein, or it may be used as a hybridization probe or PCR primer using methods disclosed below. A biologically active portion of a GmUBox1 protein can be prepared by isolating a portion of the GmUBox1 nucleotide sequences of the invention, expressing the encoded portion of the GmUBox1 protein (e.g., by recombinant expression in vitro), and assessing the activity of the encoded portion of the GmUBox1 protein. Nucleic acid molecules that are fragments of an a GmUBox1 nucleotide sequence comprise at least 16, 20, 25, 30, 40, 50, 60, 70, 80, 90, 100, 125, 150, 175, 200, 250, 300, 350, 400 etc. nucleotides, or up to the number of nucleotides present in a full-length GmUBox1 nucleotide sequences disclosed herein.

According to the invention, a GmUBox1 polypeptide produced recombinantly or by chemical synthesis, and fragments, variants, or other derivatives or analogs thereof, including fusion proteins, may be used as an immunogen to generate antibodies that recognize a GmUBox1 polypeptide. Such antibodies include but are not limited to polyclonal, monoclonal, chimeric, single chain, Fab fragments, and a Fab expression library. Such an antibody is specific for GmUBox1 proteins; it may recognize a mutant form of a GmUBox1, or wild-type GmUBox1. These antibodies can be used to alter disease resistance by inhibiting a GmUBox1 protein (e.g., anti-GmUBox1 intracellular antibodies) or for diagnostic purposes.

Various procedures known in the art may be used for the production of polyclonal antibodies to a GmUBox1 polypeptide or derivative or analog thereof. For the production of antibody, various host animals can be immunized by injection with a GmUBox1 polypeptide, or a derivative (e.g., fragment or fusion protein) thereof, including but not limited to rabbits, mice, rats, sheep, goats, etc. In one embodiment, a GmUBox1 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward a GmUBox1 polypeptide, or fragment, analog, or derivative thereof, any technique that provides for the production of antibody molecules by continuous cell lines in culture may be used. These include but are not limited to the hybridoma technique originally developed by Kohler and Milstein (Nature 256:495-497, 1975), as well as the trioma technique, the human B-cell hybridoma technique (Kozbor et al., Immunology Today 4:72, 1983; Cote et al., Proc. Natl. Acad. Sci. U.S.A. 80:2026-2030, 1983), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published 28 Dec. 1989).

In accordance with the invention, techniques described for the production of single chain antibodies (U.S. Pat. Nos. 5,476,786 and 5,132,405 to Huston; U.S. Pat. No. 4,946,778) can be adapted to produce a GmUBox1 polypeptide-specific single chain antibodies. An additional embodiment of the invention utilizes the techniques described for the construction of Fab expression libraries (Huse et al., Science 246: 1275-1281, 1989) to allow rapid and easy identification of monoclonal Fab fragments with the desired specificity for a GmUBox1 polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. GmUBox1 activity can also be inhibited by expression of anti-GmUBox1 intracellular antibodies, e.g., single chain Fv antibodies, using techniques known in the art (see generally Chen, Mol. Med. Today 3:160-167, 1997; Spitz, et al., Anticancer Res. 16:3415-3422, 1996; Indolfi et al., Nat. Med. 2:634-635, 1996; Kijima et al., Pharmacol. Ther. 68:247-267, 1995).

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a GmUBox1 polypeptide, one may assay generated hybridomas for a product which binds to a GmUBox1 polypeptide fragment containing such epitope. For selection of an antibody specific to a GmUBox1 polypeptide from a particular species of animal, one can select on the basis of positive binding with a GmUBox1 polypeptide expressed by or isolated from cells of that species of animal.

The foregoing antibodies can be used in methods known in the art relating to the localization and activity of a GmUBox1 polypeptide, e.g., for Western blotting, imaging a GmUBox1 polypeptide in situ, measuring levels thereof in appropriate physiological samples, etc., using any of the detection techniques mentioned above or known in the art. Such antibodies can also be used in assays for ligand binding, e.g., as described in U.S. Pat. No. 5,679,582. In a specific embodiment, antibodies that agonize or antagonize the activity of a GmUBox1 polypeptide can be generated. Such antibodies can be tested using the assays described infra for identifying ligands.

The proteins of the invention may be altered in various ways including amino acid substitutions, deletions, truncations, and insertions. Methods for such manipulations are generally known in the art. For example, amino acid sequence variants of the GmUBox1 proteins can be prepared by mutations in the DNA. Methods for mutagenesis and nucleotide sequence alterations are well known in the art. See, for example, Kunkel (1985) PNAS USA 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

The nucleotide sequences of the invention can be used to isolate corresponding sequences from other organisms, particularly other plants, more particularly other crop plants. In this manner, methods such as PCR, hybridization, and the like can be used to identify such sequences based on their sequence homology to the sequences set forth herein. Sequences isolated based on their sequence identity to the nucleotide sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that have a GmUBox1-like activity or and which hybridize under stringent conditions to the GmUBox1 sequences disclosed herein, or to fragments thereof, are encompassed by the present invention.

The isolation of polynucleotides of the invention may be accomplished by a number of techniques. For instance, oligonucleotide probes based on the sequences disclosed herein can be used to identify the desired polynucleotide in a cDNA or genomic DNA library from a desired plant species, for example, soybean, such as a *Phytophthora sojae*-infected etiolated hypocotyls soybean cDNA library. See, for example, Example 1. To construct genomic libraries, large segments of genomic DNA are generated by random fragmentation, e.g. using restriction endonucleases, and are ligated with vector DNA to form concatemers that can be packaged into the appropriate vector. Alternatively, cDNA libraries from plants or plant parts (e.g., flowers) may be constructed.

The cDNA or genomic library can then be screened using a probe based upon the sequence of a cloned GmUBox1 gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying genes such as GmUBox1 from plant tissues or *Phytophthora sojae*-infected etiolated hypocotyls soybean cDNA are generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). Exemplary primers are described in Example 1. The amplification conditions are typically as follows. Reaction components: 10 mM Tris-HCl, pH 8.3, 50 mM potassium chloride, 1.5 mM magnesium chloride, 0.001% gelatin, 200 μM dATP, 200 μM dCTP, 200 μM dGTP, 200 μM dTTP, 0.4 μM primers, and 100 units per ml Taq polymerase. Program: 96 C for 3 min., 30 cycles of 96 C for 45 sec., 50 C for 60 sec., 72 for 60 sec, followed by 72 C for 5 min.

Polynucleotides may also be synthesized by well-known techniques as described in the technical literature. See, e.g., Carruthers et al., Cold Spring Harbor Symp. Quant. Biol. 47:411-418 (1982), and Adams et al., J. Am. Chem. Soc. 105:661 (1983). Double stranded DNA fragments may then be obtained either by synthesizing the complementary strand and annealing the strands together under appropriate conditions, or by adding the complementary strand using DNA polymerase with an appropriate primer sequence.

The genus of GmUBox1 nucleic acid sequences of the invention includes genes and gene products identified and characterized by analysis using nucleic acid sequences of the invention, including SEQ ID NOS: 1, 2, 5 and 7 and protein sequences of the invention, including SEQ ID NOS: 3, 4 and 6. GmUBox1 sequences of the invention include nucleic acid sequences having substantial identity to SEQ ID NO: 1, 2, 5 or 7. GmUBox1 sequences of the invention also include polypeptide sequences having substantial identity to SEQ ID NO: 3, 4 or 6. Fragments and variants of the GmUBox1 polynucleotides and proteins encoded thereby can be employed in the present invention. As used herein, a GmUBox1 activity refers to an activity exerted by a GmUBox1 protein, polypeptide or portion thereof as determined in vivo, or in vitro, according to standard techniques. In one embodiment, a GmUBox1 activity is at least one or more of the following activities: (i) E3 ubiquitin ligase activity, for example, binding E2 and catalyzing the formation of an isopeptide linkage between the activated ubiquitin and the substrate protein, (ii) conferring in a plant susceptibility to a plant pathogen, such as *Phytophthora sojae*, or disease caused by a plant pathogen, such as *Phytophthora* disease such as root rot, preferably in a soybean plant, (iii) conferring in a plant susceptibility to an environmental stress such as drought, or (iv) protein-protein interaction with a pathogen Avr protein, such as Avr1b. The amino acid sequence of Avr1b is provided by Genbank accession number AF449620.1. In a preferred embodiment, decreased or decreasing GmUBox1 activity or expression results in one or more of the following activities: (i) decreased E3 ubiquitin ligase activity, for example, binding E2 and catalyzing the formation of an isopeptide linkage between the activated ubiquitin and the substrate protein as compared to the ligase activity of a control; (ii) decreasing plant susceptibility to a plant pathogen, such as *Phytophthora sojae*, or disease caused by a plant pathogen, such as *Phytophthora* disease, such as root rot, preferably in a soybean plant, as compared to the plant susceptibility to the same plant pathogen or disease caused by the plant pathogen of a control; (iii) increasing or enhancing plant resistance to a plant pathogen, such as *Phytophthora sojae*, or disease caused by a plant pathogen, such as *Phytophthora* disease, such as root rot, preferably in a soybean plant, as compared to the plant resistance to the same plant pathogen or disease caused by the plant pathogen of a control; (iv) decreasing in a plant susceptibility to an environmental stress such as drought as compared to plant susceptibility to the environmental stress of a control; (v) increasing in a plant tolerance to an environmental stress such as drought as compared to plant tolerance to the environmental stress of a control; or (vi) inhibiting protein-protein interaction with a pathogen Avr protein, such as Avr1b.

III. Use of Nucleic Acids of the Invention

A. Use of Nucleic Acids of the Invention to Inhibit or Suppress Gene Expression

The invention provides methods of modulating disease resistance in a plant by introducing into a plant a recombinant expression cassette comprising a regulatory element operably linked to a GmUBox1 polynucleotide.

The invention also provides methods for enhancing disease resistance against a pathogen in a plant by decreasing expression of a nucleic acid molecule encoding a GmUBox1gene product. In a transgenic plant of the invention, a nucleic acid molecule, or antisense constructs thereof, encoding a GmUBox1gene product can be operatively linked to an exogenous regulatory element. The invention provides, for example, a transgenic plant characterized by enhanced disease resistance to a pathogen having an expressed nucleic acid molecule encoding a GmUBox1gene product, preferably in antisense orientation, that is operatively linked to an exogenous constitutive regulatory element. In one embodiment, the invention provides a transgenic plant that is characterized by enhanced disease resistance to a pathogen and/or increased immune response due to decreased expression of a nucleic acid molecule encoding a GmUBox1 polypeptide. In some embodiments, decreased expression of GmUBox1 results in reduced ubiquitin-mediated protein degradation.

Assays that measure disease resistance activity in a plant are commonly known in the art, as are methods to quantitate disease resistance in plants following pathogen infection. See, for example, U.S. Pat. No. 5,614,395, herein incorporated by reference. These assays may be used to measure the activity or lack of activity of the polypeptides of the invention. See, for example, Examples 7 and 9. Such techniques include, measuring over time, the average lesion diameter, the pathogen biomass, and the overall percentage of decayed plant tissues or other characteristics relevant to the disease. For example, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Pathogens may include, but are not limited to, fungal, bacterial and viral pathogens for primarily soybeans which include: *Phytophthora sojae, Phytophthora infestans, Hyaloperonospora parasitica, Peronospora parasitica, Macrophomina phaseolina, Rhizoctonia solani, Sclerotinia sclerotiorum, Fusarium virguliformae, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassfcola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines*. In a preferred embodiment, the pathogen is an oomycete, including but not limited to fungi that produce oospores such as *Pythium, Phytophthora,* and *Aphanomyces*.

Viral pathogens include tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthephaseolorum* var. *sojae* (*Phomopsis sojae*), *Diaporthephaseolorum* var. *caulivora, Sclerotium rolfsii, Cercospora kikuchii, Cercospora sojina, Peronospora manshurica, Colletotrichum dematium*(*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis,* Fusar-atrum, *Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* fsp. *tritici, Puccinia recondita* fsp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* zvar. *subglutinans,*

*Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis,* Kabatie-maydis, *Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia corotovora,* Cornstunt spiroplasma, *Diplodia macrospora, Sclerophthora macrospora, Peronosclerospora sorghi, Peronosclerospora philippinensis, Peronosclerospora maydis, Peronosclerospora sacchari, Spacelotheca reiliana, Physopella zeae, Cephalosporium maydis, Caphalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root knot, cyst and lesion nematodes, etc. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus*, chinch bug; *Melanoplus femurrubrum*, redlegged grasshopper; *Melanoplus sanguinipes*, migratory grasshopper; *Hylemya platura*, seedcom maggot; *Agromyza parvicornis*, corn blot leafminer; *Anaphothrips obscrurus*, grass thrips; *Solenopsis milesta*, thief ant; *Tetranychus urticae*, twospotted spider mite; *Sorghum: Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus*, chinch bug; *Acrosternum hilare*, green stink bug; *Euschistus servus*, brown stink bug; *Delia platura*, seedcorn maggot; *Mayetiola destructor*, Hessian fly;

*Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

In another aspect, methods and compositions of the present invention may be used to provide resistance to pathogen-induced diseases in including but not limited to Bacterial blight, a disease frequently caused by *Pseudomonas amygdali* pv. *glycinea*, Bacterial crinkle-leaf, a disease frequently caused by *Pseudomonas syringae* subsp. *syringae*, Bacterial pustules, a disease frequently caused by *Xanthomonas axonopodis* pv. *glycines* or *Xanthomonas campestris* pv. *glycines*, Bacterial tan spot, a disease frequently caused by *Curtobacterium flaccumfaciens* pv. *Flaccumfaciens* or *Corynebacterium flaccumfaciens* pv. *flaccumfaciens*, Bacterial wilt, a disease frequently caused by *Curtobacterium flaccumfaciens* pv. *flaccumfaciens*, *Ralstonia solanacearum* or *Pseudomonas solanacearum*, Wildfire, a disease frequently caused by *Pseudomonas syringae* pv. *tabaci*, Alternaria leaf spot, a disease frequently caused by *Alternaria* spp., Anthracnose, a disease frequently caused by *Colletotrichum truncatum, Colletotrichum dematium* f. *truncatum, Glomerella glycines* or *Colletotrichum destructivum*, Black leaf blight, a disease frequently caused by *Arkoola nigra*, Black root rot, a disease frequently caused by *Thielaviopsis basicola, Chalara elegans*, Brown spot, a disease frequently caused by *Septoria glycines, Mycosphaerella usoenskajae*, Brown stem rot, a disease frequently caused by *Phialophora gregata, Cephalosporium gregatum*, Charcoal rot, a disease frequently caused by *Macrophomina phaseolina*, Choanephora leaf blight, a disease frequently caused by *Choanephora infundibulifera, Choanephora trispora*, Damping-off, a disease frequently caused by *Rhizoctonia solani, Thanatephorus cucumeris, Pythium aphanidermatum, Pythium debaryanum, Pythium irregulare, Pythium myriotylum* or *Pythium ultimum*, Downy mildew, a disease frequently caused by *Peronospora manshurica*, Drechslera blight, a disease frequently caused by *Drechslera glycines*, Frogeye leaf spot, a disease frequently caused by *Cercospora sojina*, Fusarium root rot, a disease frequently caused by *Fusarium* spp., Leptosphaerulina leaf spot, a disease frequently caused by *Leptosphaerulina trifolii*, Mycoleptodiscus root rot, a disease frequently caused by *Mycoleptodiscus terrestris*, Neocosmospora stem rot, a disease frequently caused by *Neocosmospora vasinfecta Acremonium* spp., Phomopsis seed decay, a disease frequently caused by *Phomopsis* spp., Phytophthora root and stem rot, a disease frequently caused by *Phytophthora sojae*, Phyllosticta leaf spot, a disease frequently caused by *Phyllosticta sojaecola*, Phymatotrichum root rot (cotton root rot), a disease frequently caused by *Phymatotrichopsis omnivora, Phymatotrichum omnivorum*, Pod and stem blight, a disease frequently caused by *Diaporthe phaseolorum, Phomopsis sojae*, Powdery mildew, a disease frequently caused by *Microsphaera diffusa*, Purple seed stain, a disease frequently caused by *Cercospora kikuchii*, Pyrenochaeta leaf spot, a disease frequently caused by *Pyrenochaeta glycines*, Pythium rot, a disease frequently caused by *Pythium aphanidermatum, Pythium debaryanum, Pythium irregulare, Pythium myriotylum* or *Pythium ultimum*, Red crown rot, a disease frequently caused by *Cylindrocladium crotalariae* or *Calonectria crotalariae*, Red leaf blotch (Dactuliophora leaf spot), a disease frequently caused by *Dactuliochaeta glycines, Pyrenochaeta glycines* or *Dactuliophora glycines*, Rhizoctonia aerial blight, a disease frequently caused by *Rhizoctonia solani* or *Thanatephorus cucumeris*, Rhizoctonia root and stem rot, a disease frequently caused by *Rhizoctonia solani*, Rust, a disease frequently caused by *Phakopsora pachyrhizi*, Scab, a disease frequently caused by *Spaceloma glycines*, Sclerotinia stem rot, a disease frequently caused by *Sclerotinia sclerotiorum*, Southern blight (damping-off and stem rot, Sclerotium blight), a disease frequently caused by *Sclerotium rolfsii* or *Athelia rolfsii*, Stem canker, a disease frequently caused by *Diaporthe phaseolorum, Diaporthe phaseolorum* var. *caulivora* or *Phomopsis phaseoli*, Stemphylium leaf blight, a disease frequently caused by *Stemphylium botryosum* or *Pleospora tarda*, Sudden death syndrome, a disease frequently caused by *Fusarium solani* f.sp. *glycines*, Target spot, a disease frequently caused by *Corynespora cassiicola*, Yeast spot, a disease frequently caused by *Nematospora coryli*, Lance nematode, a disease frequently caused by *Hoplolaimus columbus, Hoplolaimus galeatus* or *Hoplolaimus magnistylus*, Lesion nematode, a disease frequently caused by *Pratylenchus* spp., Pin nematode, a disease frequently caused by *Paratylenchus projectus* or *Paratylenchus tenuicaudatus*, Reniform nematode, a disease frequently caused by *Rotylenchulus reniformis*, Ring nematode, a disease frequently caused by *Criconemella ornata*, Root-knot nematode, a disease frequently caused by *Meloidogyne arenaria, Meloidogyne hapla, Meloidogyne incognita* or *Meloidogyne javanica*, Sheath nematode, a disease frequently caused by *Hemicycliophora* spp., Soybean cyst nematode, a disease frequently caused by *Heterodera glycines*, Spiral nematode, a disease frequently caused by *Helicotylenchus* spp., Sting nematode, a disease frequently caused by *Belonolainus gracilis* or *Belonolainus longicaudatus*, Stubby root nematode, a disease frequently caused by *Paratrichodorus minor*, Stunt nematode, a disease frequently caused by *Quinisulcius acutus* or *Tylenchorhynchus* spp., Alfalfa mosaic, a disease frequently caused by genus Alfamovirus, Alfalfa mosaic virus (AMV), Bean pod mottle, a disease frequently caused by genus Comovirus, Bean pod mottle virus (BPMV), Bean yellow mosaic, a disease frequently caused by genus Potyvirus, Bean yellow mosaic virus (BYMV), Brazilian bud blight, a disease frequently caused by genus Ilarvirus, Tobacco streak virus (TSV), Cowpea chlorotic mottle, a disease frequently caused by genus Bromovirus, Cowpea chlorotic mottle virus (CCMV), Mung bean yellow mosaic, a disease frequently caused by genus Begomovirus, Mung bean yellow mosaic virus (MYMV), Peanut mottle, a disease frequently caused by genus Potyvirus, Peanut mottle virus (PeMoV), Peanut stripe, a disease frequently caused by genus Potyvirus, Peanut stripe virus (PStV), Peanut stunt, a disease frequently caused by genus Cucumovirus, Peanut stunt virus (PSV), Soybean chlorotic mottle, a disease frequently caused by genus Caulimovirus, Soybean chlorotic mottle virus (SbCMV), Soybean crinkle leaf, a disease frequently caused by genus Begomovirus, Soybean crinkle leaf virus (SCLV), Soybean dwarf, a disease frequently caused by genus Luteovirus, Soybean dwarf virus (SbDV), Soybean mosaic, a disease frequently caused by genus Potyvirus, Soybean mosaic virus (SMV), Soybean severe stunt, a disease frequently caused by genus Nepovirus, Soybean severe stunt virus (SSSV), Tobacco ringspot (bud blight), a disease frequently caused by genus Nepovirus, Tobacco ringspot virus (TRSV).

It is understood in the art that plant DNA viruses and fungal pathogens remodel the control of the host replication and gene expression machinery to accomplish their own replication and effective infection. The plant response to stress, such as stress caused by *Phytophthora* attack, is known to involve many basic biochemical pathways and cellular functions. Hence, the sequences of the invention may find use in altering the defense mechanisms of a host plant, for example, the immune response, to provide broad-based resistance to disease or insect pests. Additionally, the present invention may be useful in preventing corruption of the plant's immune response by viruses and other plant pathogens. The present invention also provides methods of modifying stress tolerance of a plant comprising, modifying the expression of a GmUBox1 nucleic acid of the present invention in the plant. The invention provides that this method can be performed such that the stress tolerance is either increased or decreased. Preferably, stress tolerance is increased in a plant via eliminating or decreasing expression or activity of a GmUBox1 nucleic acid or polypeptide.

The compositions and methods of the invention may in one aspect function to suppress plant diseases as described elsewhere herein. The cells that have been transformed may be grown into plants in accordance with conventional ways. See, for example, McCormick et al. (1986) *Plant Cell Reports* 5:8184. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The invention in one aspect comprises expression constructs comprising a DNA sequence which encodes upon expression a GmUBox1 gene product operably linked to a promoter to direct expression of the protein. The polynucleotide may be in sense or antisense orientation, preferably antisense orientation. These constructs are then introduced into plant cells using standard molecular biology techniques. The invention can be also be used for hybrid plant or seed production, once transgenic inbred parental lines have been established.

In another aspect the invention involves the inhibition of the regulatory gene product in plants through introduction of a construct designed to inhibit the same gene product. The design and introduction of such constructs based upon known DNA sequences is known in the art and includes such technologies as antisense RNA or DNA, co-suppression or any other such mechanism. Several of these mechanisms are described and disclosed in U.S. Pat. No. 5,686,649 to Chua et. al, which is hereby expressly incorporated herein by reference.

The methods of the invention described herein may be applicable to any species of plant, including for example, soybean, *Arabidopsis*, corn, sunflower, sorghum, canola, wheat, alfalfa, cotton, rice, barley and millet.

The GmUBox1 sequences of the invention can be used to prepare expression cassettes useful in a number of techniques, including inhibiting, suppressing or increasing expression or for ectopic expression. A number of methods can be used to decrease or inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., Proc. Nat. Acad. Sci. USA, 85:8805-8809 (1988); Pnueli et al., The Plant Cell 6:175-186 (1994); and Hiatt et al., U.S. Pat. No. 4,801,340.

As described herein, in some embodiments, it is contemplated that the nucleic acids encoding a GmUBox1 polypeptide of the present invention may be utilized to decrease the level of GmUBox1 mRNA and/or protein in transfected cells as compared to the levels in wild-type cells. In some of these embodiments, the nucleic acid sequence encoding a GmUBox1 protein of the present invention is used to design a nucleic acid sequence encoding a nucleic acid product which interferes with the expression of the nucleic acid encoding a GmUBox1 polypeptide.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of GmUBox1 can be useful for producing a plant in which GmUBox1 expression is decreased or suppressed. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of GmUBox1 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. Nature, 334:585-591 (1988).

Another method of suppression, decreased expression, is sense suppression (also known as co-suppression). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (e.g., Napoli et al. (1990) Plant Cell 2:279-289; van der Krol et al. (1990) Plant Cell 2:291-299; Smith et al. (1990) Mol. Gen. Genetics 224:477-481). Accordingly, in some embodiments the nucleic acid sequences encoding a GmUBox1 of the present invention are expressed in another species of plant to effect cosuppression of a homologous gene. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., The Plant Cell 2:279-289 (1990); Flavell, Proc. Natl. Acad. Sci., USA 91:3490-3496 (1994); Kooter and Mol, Current Opin. Biol. 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Endogenous gene expression may also be suppressed or decreased by means of RNA interference (RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., Proc. Natl. Acad. Sci. USA 97: 4985 (2000); Waterhouse et al., Proc. Natl. Acad. Sci. USA 95:13959-13964 (1998); Tabara et al. Science 282:430-431 (1998)). For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. An effective method to down regulate a gene is by hairpin RNA constructs. Guidance to the design of such constructs for efficient, effective and high throughput gene silencing have been described (Wesley S V et al. (2001) Plant J. 27: 581-590). Another method to decrease expression of a gene (either endogenous or exogenous) is via siRNAs. siRNAs can be applied to a plant and taken up by plant cells; alternatively, siRNAs can be expressed in vivo from an expression cassette.

The resulting plants may then be screened for a phenotype associated with the target protein and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 50, 100, 150, 200, or more nucleotides in length. In some cases, fragments for use in RNAi will be at least substantially similar to regions of a target protein, e.g. a GmUBox1 protein of the invention, that do not occur in other proteins in the organism or may be selected to have as little similarity to other organism transcripts as possible, e.g., selected by comparison to sequences in analyzing publicly-available sequence databases, e.g. GenBank (NCBI).

Expression vectors that continually express siRNA in transiently- and stably-transfected have been engineered to express small hairpin RNAs, which get processed in vivo into siRNAs molecules capable of carrying out gene-specific silencing (Brummelkamp et al., Science 296:550-553 (2002), and Paddison, et al., Genes & Dev. 16:948-958 (2002)). Post-transcriptional gene silencing by double-stranded RNA is discussed in further detail by Hammond et al. Nature Rev Gen 2: 110-119 (2001), Fire et al. Nature 391: 806-811 (1998) and Timmons and Fire Nature 395: 854 (1998).

One of skill in the art will recognize that using technology based on specific nucleotide sequences (e.g., antisense or sense suppression technology), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variance between family members.

Another means of inhibiting GmUBox1 function in a plant is by creation of dominant negative mutations. In this approach, non-functional, mutant GmUBox1 polypeptides are introduced into a plant. A dominant negative construct also can be used to suppress GmUBox1 expression in a plant.

One skilled in the art understands that a construct including a dominant negative GmUBox1 of the present invention can be used to suppress in a plant GmUBox1 activity, for example, of a GmUBox1 protein of the present invention. See, for example, a carboxy-terminal deletion mutant of AGAMOUS was used as a dominant negative construct to suppress expression of the MADS box gene AGAMOUS (Mizukami et al., Plant Cell 8:831-844 (1996)). GmUBox1 function can be suppressed in soybean by creation of dominant negative mutations. In this approach, non-functional, mutant GmUBox1 polypeptides are introduced into a plant.

A dominant negative construct also can be used to suppress the function or activity of GmUBox1 in a plant. A dominant negative construct useful in the invention generally contains a portion of the complete GmUBox1 coding sequence sufficient to allow for a protein-protein interaction with the pathogen Avr protein such as *P. sojae* Avr1b but with no E3 ligase activity. See, e.g. Avr1b, Genbank accession number AF449620.1. In this way, the dominant negative mutant competes with the wild type GmUBox1 protein and does not allow the wild type protein to participate in the ubiquitin-mediated protein degradation pathway. For example, a GmUBox1 dominant negative mutant may be created so that it contains a mutated activation domain but still is able to bind to pathogen effector protein (e.g. *P. sojae* Avr1b). See, for example, Example 6. As shown in Example 1, the UBox domain is not required for interaction with Avr1b. This truncated GmUBox1 is suitable for overexpression of the mutant version of the protein to create a dominant mutant phenotype; because, without wishing to be bound by this theory, it is believed that in the presence of high concentration of this mutant protein the wild type protein will fail to bind to pathogen effector protein and to act on its substrate following infection. Thus, there will be no manipulation of the soybean cells by the pathogen protein.

Accordingly there are many techniques that can be used to decrease expression or activity of a GmUBox1 polypeptide of the present invention. In some embodiments, expression or activity of both GmUBox1-1 and GmUBox1-2 are decreased in a plant. Decreased or decreasing expression of a GmUBox1 polypeptide in a plant refers to the protein level of the GmUBox1 polypeptide in a plant as compared to the protein level of the same GmUBox1 polypeptide in a control plant, for example, where the corresponding GmUBox1 gene has not been mutated or modified or where the plant cell has not been transformed with a polynucleotide of the present invention.

Expression of the GmUBox1 polypeptide may be decreased as compared to the expression of the corresponding GmUBox1 polypeptide in a control, for example, expression may be decreased by 5%, 10%, 15%, 20%, 25%, 30%, 35%, 40%, 45%, 50% or more. The expression level of the GmUBox1 polypeptide may be measured, for example, by assaying for the level of GmUBox1 polypeptide expressed in the plant cell or plant using Western blot or other techniques known to one skilled in the art.

Expression of the GmUBox1 polynucleotide may be decreased as compared to the expression of the corresponding GmUBox1 polynucleotide in a control, for example, expression may be decreased by 5%, 10%, 15%, 20%, 25%, 30%, 35%, 40%, 45%, 50% or more. The expression level of the GmUBox1 polynucleotide may be measured, for example, by assaying for the level of GmUBox1 polynucleotide expressed in the plant cell or plant using Northern blot or other techniques known to one skilled in the art. In particular, the level of transcription of the gene (an indicator of the amount of mRNA available for translation to the gene product) may be ascertained by performing a Northern blot or quantitative rt-PCR (for reference see, for example, Ausubel et al., 1988 Current Protocols in Molecular Biology, Wiley: New York). Total cellular RNA can be prepared from cells, tissues or organs by several methods, all well-known in the art. Bormann, E. R. et al., 1992 Mol. Microbiol. 6:317 326.

In other embodiments of the invention, the activity of one or more of the GmUBox1 polypeptides is decreased or eliminated. Decreased or decreasing activity of a GmUBox1 polypeptide in a plant refers to the activity of the GmUBox1 polypeptide in a plant as compared to the activity of the same GmUBox1 polypeptide in a control plant, for example, where the corresponding GmUBox1 gene has not been mutated or modified or where the plant cell has not been transformed with a polynucleotide of the present invention or a construct expressing a dominant negative GmUBox1. Activity of the GmUBox1 polypeptide may be decreased as compared to the activity of the corresponding GmUBox1 polypeptide in a control, for example, activity may be decreased by 5%, 10%, 15%, 20%, 25%, 30%, 35%, 40%, 45%, 50% or more. The activity of the GmUBox1 polypeptide may be measured, for example, by assaying for the activity of the GmUBox1 polypeptide using techniques known to one skilled in the art, e.g. in vitro self-ubiquitination or ligase assays. (Cho, S. K., Ryu, M. Y., Song, C., Kwak, J. M. and Kim, W. T. (2008) *Arabidopsis* PUB22 and PUB23 are homologous U-Box E3 ubiquitin ligases that play combinatory roles in response to drought stress. *The Plant cell,* 20, 1899-1914. Gonzalez-Lamothe, R., Tsitsigiannis, D. I., Ludwig, A. A., Panicot, M., Shirasu, K. and Jones, J. D. (2006) The U-box protein CMPG1 is required for efficient activation of defense mechanisms triggered by multiple resistance genes in tobacco and tomato. *Plant Cell,* 18, 1067-1083.) See, for example, Example 7.

B. Use of Nucleic Acids of the Invention to Enhance Gene Expression

Isolated sequences prepared as described herein can also be used to prepare expression cassettes that enhance or increase endogenous GmUBox1 gene expression. Where overexpression of a gene is desired, the desired gene from a different species may be used to decrease potential sense suppression effects. Enhanced expression of GmUBox1 polynucleotides is useful, for example, to produce plants with increased GmUBox1-mediated ligase ubiquitin-mediated protein degradation.

Any of a number of means well known in the art can be used to increase GmUBox1 activity in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, one or several GmUBox1 genes can be expressed constitutively (e.g., using the CaMV 35S promoter).

C. Modification of Endogenous GmUBox1 Genes

Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used.

Modified protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski, et al., (1991). Meth. Enzymol. 194: 302-318). For example, the chains can vary from the naturally occurring sequence at the primary structure level by amino acid substitutions, additions, deletions, and the like. These modifications can be used in a number of combinations to produce the final modified protein chain.

Alternatively, homologous recombination can be used to induce targeted gene modifications by specifically targeting the GmUBox1 gene in vivo (see, generally, Grewal and Klar, Genetics 146: 1221-1238 (1997) and Xu et al., Genes Dev. 10: 2411-2422 (1996)). Accordingly, in some embodiments, one or more GmUBox genes encoding GmUBox1's of the present invention, e.g. GmUBox1-1 or GmUBox1-2 or both, may be modified in the genome so that it is disrupted, e.g. as a knock out, or mutated so expression of the gene or activity of the expressed protein is decreased as compared to the expression or activity in a plant that does not have one or more GmUBox genes of the present invention modified. Homologous recombination has been demonstrated in plants (Puchta et al., Experientia 50: 277-284 (1994), Swoboda et al., EMBO J. 13: 484-489 (1994); Offringa et al., Proc. Natl. Acad. Sci. USA 90: 7346-7350 (1993); and Kempin et al. Nature 389:802-803 (1997)).

In applying homologous recombination technology to the genes of the invention, mutations in selected portions of a GmUBox1 gene sequences (including 5' upstream, 3' downstream, and intragenic regions) such as those disclosed herein are made in vitro and then introduced into the desired plant using standard techniques. Since the efficiency of homologous recombination is known to be dependent on the vectors used, use of dicistronic gene targeting vectors as described by Mountford et al., Proc. Natl. Acad. Sci. USA 91: 4303-4307 (1994); and Vaulont et al., Transgenic Res. 4: 247-255 (1995) are conveniently used to increase the efficiency of selecting for altered GmUBox1 gene expression in transgenic plants. The mutated gene will interact with the target wild-type gene in such a way that homologous recombination and targeted replacement of the wild-type gene will occur in transgenic plant cells, resulting in suppression, decreased expression, of GmUBox1 activity.

Alternatively, oligonucleotides composed of a contiguous stretch of RNA and DNA residues in a duplex conformation with double hairpin caps on the ends can be used. The RNA/DNA sequence is designed to align with the sequence of the target GmUBox1 gene and to contain the desired nucleotide change. Introduction of the chimeric oligonucleotide on an extrachromosomal T-DNA plasmid results in efficient and specific GmUBox1 gene conversion directed by chimeric molecules in a small number of transformed plant cells. This method is described in Cole-Strauss et al., Science 273:1386-1389 (1996) and Yoon et al., Proc. Natl. Acad. Sci. USA 93: 2071-2076 (1996).

D. Screening

Nucleic acid molecules corresponding to natural allelic variants and analogs, orthologs, and paralogs of a GmUBox1 cDNA can be isolated based on their identity to the GmUBox1 nucleic acids described herein using GmUBox1 cDNAs, or a portion thereof, as a hybridization probe according to standard hybridization techniques under stringent hybridization conditions. In an alternative embodiment, homologs of the GmUBox1 can be identified by screening combinatorial libraries of mutants, e.g., truncation mutants, of the GmUBox1 for GmUBox1 activity. In one embodiment, a variegated library of GmUBox1 variants is generated by combinatorial mutagenesis at the nucleic acid level and is encoded by a variegated gene library. A variegated library of GmUBox1 variants can be produced by, for example, enzymatically ligating a mixture of synthetic oligonucleotides into gene sequences such that a degenerate set of potential GmUBox1 sequences is expressible as individual polypeptides, or alternatively, as a set of larger fusion polypeptides (e.g., for phage display) containing the set of GmUBox1 sequences therein. There are a variety of methods that can be used to produce libraries of potential GmUBox1 homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential GmUBox1 sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477).

In addition, libraries of fragments of the GmUBox1 coding regions can be used to generate a variegated population of GmUBox1 fragments for screening and subsequent selection of homologs of a GmUBox1. In one embodiment, a library of coding sequence fragments can be generated by treating a double stranded PCR fragment of a GmUBox1 coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the GmUBox1.

Several techniques are known in the art for screening gene products of combinatorial libraries made by point mutations or truncation, and for screening cDNA libraries, such as *Phytophthora sojae*-infected etiolated hypocotyls soybean cDNA library, for gene products having a selected property. Such techniques are adaptable for rapid screening of the gene libraries generated by the combinatorial mutagenesis of GmUBox1 homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify GmUBox1 homologs (Arkin and Yourvan, 1992 PNAS 89:7811 7815; Delgrave et al., 1993 Polypeptide Engineering 6(3):327 331). In another embodiment, cell based assays can be exploited to analyze a variegated GmUBox1 library, using methods well known in the art. The present invention further provides a method of identifying a novel GmUBox1, comprising (a) raising a specific antibody response to a GmUBox1, or a fragment thereof, for example, as described herein; (b) screening putative GmUBox1 material with the antibody, wherein specific binding of the antibody to the material indicates the presence of a potentially novel GmUBox1; and (c) analyzing the bound material in comparison to a known GmUBox1, to determine its novelty.

The present invention further provides methods of identifying or screening for proteins which interact with GmUBox1 proteins, or derivatives, fragments, mutants or analogs thereof. Any method suitable for detecting protein-protein interactions can be employed for identifying novel GmUBox1 protein-protein interactions. Among the traditional methods which can be employed are co-immunoprecipitation, crosslinking and co-purification through gradients or chromatographic columns. Utilizing procedures such as these allows for the identification of proteins that interact with a GmUBox1 polypeptide. Once identified, such proteins can be used, for example, to disrupt GmUBox1 activity, thereby decreasing GmUBox1 activity, and for example, increasing resistance in a plant to a disease caused by a pathogen, such as an oomycete pathogen. Once identified, such proteins that interact with a GmUBox1 polypeptide can also be used, in conjunction with standard techniques, to identify the corresponding gene that encodes the protein which interacts with the GmUBox1 polypeptide. For example, at least a portion of the amino acid sequence of the polypeptide can be ascertained using techniques well known to those of skill in the art, such as via the Edman degradation technique (see, e.g., Creighton, 1983, Proteins: Structures and Molecular Principles, W.H. Freeman & Co., N.Y., pp. 34-49). The amino acid sequence obtained can be used as a guide for the generation of oligonucleotide mixtures that can be used to screen for gene sequences. Screening can be accomplished, for example, by standard hybridization or PCR techniques. Techniques for the generation of oligonucleotide mixtures and for screening are well-known. (See, e.g., Ausubel, supra., and PCR Protocols: A Guide to Methods and Applications, 1990, Innis, M. et al., eds. Academic Press, Inc., New York).

Additionally, methods can be employed which result in the simultaneous identification of genes which encode proteins interacting with a GmUBox1 polypeptide. These methods include, for example, probing expression libraries with labeled GmUBox1 polypeptide, using this protein in a manner similar to the well known technique of antibody probing of lambda gt11 libraries.

One method which detects protein interactions in vivo, the two-hybrid system, is described in detail for illustration purposes only and not by way of limitation. One version of this system has been described (Chien et al., 1991, Proc. Natl. Aca. Sci. U.S.A. 88:9578-9582) and is commercially available from Clontech (Palo Alto, Calif.). Briefly, utilizing such, a system, plasmids are constructed that encode two hybrid proteins: one consists of the DNA-binding domain of a transcription activator protein fused to a known protein, in this case, an GmUBox1 polypeptide, and the other consists of the activator protein's activation domain fused to an unknown protein that is encoded by a cDNA, in this example preferably a soybean cDNA, which has been cloned as a activation domain fusion into a plasmid as a part of a cDNA library. The plasmids are transformed into a strain of the yeast *Saccharomyces cerevisiae* that contains a reporter gene (e.g., lacZ) whose regulatory region contains the transcription activator's binding sites. Either hybrid protein alone cannot activate transcription of the reporter gene, the DNA-binding domain hybrid cannot because it does not provide activation function, and the activation domain hybrid cannot because it cannot localize to the activator's DNA binding sites. Interaction of the two hybrid proteins reconstitutes the functional activator protein and results in expression of the reporter gene, which is detected by an assay for the reporter polypeptide.

The two-hybrid system or related methodology can be used to screen activation domain libraries for proteins that interact with a known "bait" polypeptide. By way of example, and not by way of limitation, GmUBox1 polypeptides can be used as the bait polypeptides. In a preferred embodiment, the entire GmUBox1 sequence is used as bait. Total cDNA sequences are fused to the DNA encoding an activation domain. This library and a plasmid encoding a hybrid of the bait polypeptide fused to the DNA-binding domain are co-transformed into a yeast reporter strain, and the resulting transformants are screened for those that express the reporter gene. For example, and not by way of limitation, the bait (e.g., GmUBox1) gene or cDNA can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait (e.g., GmUBox1) polypeptide are to be detected can be made using methods routinely practiced in the art. According to the particular system described herein, for example, the cDNA fragments can be inserted into a vector such that they are translationally fused to the activation domain of GAL4. This library can be co-transformed along with the bait gene-GAL4 fusion plasmid into a yeast strain which contains a lacZ gene driven by a promoter which contains GAL4 activation sequence. A cDNA encoded protein, fused to GAL4 activation domain, that interacts with bait polypeptide will reconstitute an active GAL4 protein and thereby drive expression of the lacZ gene. Colonies which express lacZ can be detected by their blue color in the presence of X-gal. The cDNA can then be purified from these strains, and used to produce and isolate the bait gene-interacting protein using techniques routinely practiced in the art.

The GmUBox1 polypeptides of the invention may, in vivo or in vitro, interact with one or more proteins, such as Avr or pathogen effector proteins or E2 proteins, most importantly substrates that are ubiquitinated by GmUBox1. Without wishing to be bound by this theory, the substrates of GmUBox1 are expected to be the master regulators of defense pathway involved in protection of plants from pathogen and pest attack.

IV. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. Ann. Rev. Genet. 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

The constructs and polynucleotides used in the methods of the invention may use any suitable promoter that expresses in the desired plant or plant cell. A number of promoters can be used in the practice of the invention. The promoters can be selected based on the desired outcome, for example, those that achieve the expression level, temporal or spatial expression pattern desired. These may include but are not limited to a native promoter, a tissue specific promoter, an inducible promoter or a constitutive promoter.

In some embodiments, the promoters derived from the GmUBox1 genes of the invention can be used to drive expression of heterologous genes. Typically, desired promoters are identified by analyzing the 5' sequences of a genomic clone corresponding to the GmUBox1 genes described here. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing et al., in GENETIC ENGINEERING IN PLANTS, pp. 221-227 (Kosage, Meredith and Hollaender, eds. (1983)).

A number of methods are known to those of skill in the art for identifying and characterizing promoter regions in plant genomic DNA (see, e.g., Jordano, et al., Plant Cell, 1: 855-866 (1989); Bustos, et al., Plant Cell, 1:839-854 (1989); Green, et al., EMBO J. 7, 4035-4044 (1988); Meier, et al., Plant Cell, 3, 309-316 (1991); and Zhang, et al., Plant Physiology 110: 1069-1079 (1996)).

In some embodiments, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

A large number of suitable promoter systems are available. For example one constitutive promoter useful for the invention is the cauliflower mosaic virus (CaMV) 35S. It has been shown to be highly active in many plant organs and during many stages of development when integrated into the genome of transgenic plants and has been shown to confer expression in protoplasts of both dicots and monocots.

The promoter used in the method or composition of the invention may be an inducible promoter. An inducible promoter is a promoter that is capable of directly or indirectly activating transcription of a DNA sequence in response to an inducer. In the absence of an inducer, the DNA sequence will not be transcribed. Typically, the protein factor that binds specifically to an inducible promoter to activate transcription is present in an inactive form which is then directly or indirectly converted to the active form by the inducer. The inducer may be a chemical agent such as a protein, metabolite (sugar, alcohol etc.), a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating, or similar methods. Examples of inducible promoters include the inducible 70 kd heat shock promoter of *D. melanogaster* (Freeling, M., Bennet, D.C., Maize ADN 1, *Ann. Rev. of Genetics,* 19:297-323) and the alcohol dehydrogenase promoter which is induced by ethanol (Nagao, R. T., et al., Miflin, B. J., Ed. Oxford Surveys of Plant Molecular and Cell Biology, Vol. 3, p. 384-438, University Press, Oxford 1986) or the Lex A promoter which is triggered with chemical treatment and is available through Ligand pharmaceuticals. The inducible promoter may be in an induced state throughout seed formation or at least for a period which corresponds to the transcription of the DNA sequence of the recombinant DNA molecule(s).

Another example of an inducible promoter is the chemically inducible gene promoter sequence isolated from a 27 kd subunit of the maize glutathione-S-transferase (GST II) gene. Two of the inducers for this promoter are N,N-diallyl-2,2-dichloroacetamide (common name: dichloramid) or benzyl-=2-chloro-4-(trifluoromethyl)-5-thiazolecarboxylate (common name: flurazole). In addition, a number of other potential inducers may be used with this promoter as described in published PCT Application No. PCT/GB90/00110 by ICI.

Another example of an inducible promoter is the light inducible chlorophyll a/b binding protein (CAB) promoter, also described in published PCT Application No. PCT/GB90/00110 by ICI. Inducible promoters have also been described in published Application No. EP89/103888.7 by Ciba-Geigy. In this application, a number of inducible promoters are identified, including the PR protein genes, especially the tobacco PR protein genes, such as PR-1a, PR-1b, PR-1c, PR-1, PR-A, PR-S, the cucumber chitinase gene, and the acidic and basic tobacco beta-1,3-glucanase genes. There are numerous potential inducers for these promoters, as described in Application No. EP89/103888.7.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. As noted above, the promoters from the GmUBox1 genes described here are particularly useful for directing gene expression so that a desired gene product is located in the valve margin of fruit. Other suitable promoters include those from genes such as SHP1 or SHP2 (Savidge, B., Rounsley, S. D., and Yanofsky, M. F. (1995) Plant Cell 7: 721-733). Examples of environmental conditions that may affect transcription by inducible promoters include anaerobic conditions, elevated temperature, or the presence of light.

Organ-specific promoters are also well known. For example, the E8 promoter is only transcriptionally activated during tomato fruit ripening, and can be used to target gene expression in ripening tomato fruit (Deikman and Fischer, *EMBO J.* (1988) 7:3315; Giovannoni et al., *The Plant Cell* (1989) 1:53). The activity of the E8 promoter is not limited to tomato fruit, but is thought to be compatible with any system wherein ethylene activates biological processes. Similarly the Lipoxegenase ("the LOX gene") is a fruit specific promoter.

Other fruit specific promoters are the 1.45 promoter fragment disclosed in Bird, et al., *Plant Mol. Bio.*, pp 651-663 (1988) and the polygalacturonase promoter from tomato disclosed in U.S. Pat. No. 5,413,937 to Bridges et al.

Leaf specific promoters include as the AS-1 promoter disclosed in U.S. Pat. No. 5,256,558 to Coruzzi and the RBCS-3A promoter isolated from pea the RBCS-3A gene disclosed in U.S. Pat. No. 5,023,179 to Lam et al.

Other examples of promoters include maternal tissue promoters such as seed coat, pericarp and ovule. Promoters highly expressed early in endosperm development are most effective in this application. Of particular interest is the promoter from the a' subunit of the soybean β-conglycinin gene [Walling et al., *Proc. Natl. Acad. Sci. USA* 83:2123-2127 (1986)] which is expressed early in seed development in the endosperm and the embryo.

Further seed specific promoters include the Napin promoter described in U.S. Pat. No. 5,110,728 to Calgene, which describes and discloses the use of the napin promoter in directing the expression to seed tissue of an acyl carrier protein to enhance seed oil production; the DC3 promoter from carrots which is early to mid embryo specific and is disclosed at *Plant Physiology*, October 1992 100(2) p. 576-581, "Hormonal and Environmental Regulation of the Carrot Lea-class Gene Dc 3, and *Plant Mol. Biol.*, April 1992, 18(6) p. 1049-1063, "Transcriptional Regulation of a Seed Specific Carrot Gene, DC 8": the phaseolin promoter described in U.S. Pat. No. 5,504,200 to Mycogen which discloses the gene sequence and regulatory regions for phaseolin, a protein isolated from *P. vulgaris* which is expressed only while the seed is developing within the pod, and only in tissues involved in seed generation.

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, *Trans. R. Soc. London* (1986) B314-343. mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al., *Plant Molecular Biology* (1984) 3:385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

Another very important method that can be used to identify cell type specific promoters that allow even to identification of genes expressed in a single cell is enhancer detection (O'Kane, C., and Gehring, W. J. (1987), "Detection in situ of genomic regulatory elements in *Drosophila*", *Proc. Natl. Acad. Sci. USA*, 84, 9123-9127). This method was first developed in *Drosophila* and rapidly adapted to mice and plants (Wilson, C., Pearson, R. K., Bellen, H. J., O'Kane, C. J., Grossniklaus, U., and Gehring, W. J. (1989), "P-element-mediated enhancer detection: an efficient method for isolating and characterizing developmentally regulated genes in *Drosophila*", *Genes & Dev.*, 3, 1301-1313; Skarnes, W. C. (1990), "Entrapment vectors: a new tool for mammalian genetics", *Biotechnology*, 8, 827-831; Topping, J. F., Wei, W., and Lindsey, K. (1991), "Functional tagging of regulatory elements in the plant genome", *Development*, 112, 1009-1019; Sundaresan, V., Springer, P. S., Volpe, T., Haward, S., Jones, J. D. G., Dean, C., Ma, H., and Martienssen, R. A., (1995), "Patterns of gene action in plant development revealed by enhancer trap and gene trap transposable elements", *Genes & Dev.*, 9, 1797-1810).

The promoter used in the method or composition of the invention may be a root specific promoter, for example, the CamV 35S promoter disclosed in U.S. Pat. No. 391,725 to Coruzzi et al; the RB7 promoter disclosed in U.S. Pat. No. 5,459,252 to Conking et al and the promoter isolated from *Brassica napus* disclosed in U.S. Pat. No. 5,401,836 to Bazc-zynski et al. which give root specific expression.

The preferred promoters may be used in conjunction with naturally occurring flanking coding or transcribed sequences of the feronia regulatory genes or with any other coding or transcribed sequence that is critical to pollen tube formation and/or fertilization.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to female gametophyte development and/or function.

Additionally, regions of one promoter may be joined to regions from a different promoter in order to obtain the desired promoter activity resulting in a chimeric promoter. Synthetic promoters which regulate gene expression may also be used.

The expression system may be further optimized by employing supplemental elements such as transcription terminators and/or enhancer elements. In one aspect, the nucleic acids of the invention may be genetically engineered to optimize expression in a given host, such as a plant cell, preferably a soybean plant cell.

A. Other Regulatory Elements

In addition to a promoter sequence, an expression cassette or construct should also contain a transcription termination region downstream of the structural gene to provide for efficient termination. The termination region or polyadenylation signal may be obtained from the same gene as the promoter sequence or may be obtained from different genes. Polyadenylation sequences include, but are not limited to the *Agrobacterium* octopine synthase signal (Gielen et al., *EMBO J.* (1984) 3:835-846) or the nopaline synthase signal (Depicker et al., *Mol. and Appl. Genet.* (1982) 1:561-573).

B. Marker Genes

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed plant. Polymerase chain reactions are also used to identify the presence of a transgene or expression using reverse transcriptase PCR amplification to monitor expression and PCR on genomic DNA. Other commonly used selection markers include the ampicillin resistance gene, the tetracycline resistance and the hygromycin resistance gene. Transformed plant cells thus selected can be induced to differentiate into plant structures which will eventually yield whole plants. It is to be understood that a selection marker gene may also be native to a plant.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

GmUBox1 nucleic acid sequences of the invention are expressed recombinantly in plant cells to decrease levels of endogenous GmUBox1 polypeptides, for example, antisense or other GmUBox1 constructs (described above) may be used to suppress GmUBox1 levels of expression. Alternatively, GmUBox1 nucleic acid sequences of the invention are expressed recombinantly in plant cells to increase levels of endogenous GmUBox1 polypeptides. A variety of different expression constructs, such as expression cassettes and vectors suitable for transformation of plant cells can be prepared. Techniques for transforming a wide variety of higher plant species are well known and described in the technical and scientific literature. See, e.g., Weising et al. Ann. Rev. Genet. 22:421-477 (1988). A DNA sequence coding for a GmUBox1 polypeptide, e.g., a cDNA sequence encoding a full length protein, can be combined with cis-acting (promoter) and trans-acting (enhancer) transcriptional regulatory sequences to direct the timing, tissue type and levels of transcription in the intended tissues of the transformed plant. Translational control elements can also be used.

The invention provides a GmUBox1 nucleic acid operably linked to a promoter which, in a preferred embodiment, is capable of driving the transcription of the GmUBox1 coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal. Typically, as discussed above, desired promoters are identified by analyzing the 5' sequences of a genomic clone corresponding to the GmUBox1 genes described here.

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment or *Agrobacterium tumefaciens*-mediated transformation techniques.

The invention in one aspect comprises expression constructs comprising a DNA sequence which encodes upon expression a GmUBox1 gene product operably linked to a promoter to direct expression of the protein. In another aspect the invention involves the inhibition of the regulatory gene product in plants through introduction of a construct designed to inhibit the same gene product, for example, an antisense sequence to GmUBox1 polynucleotides of the present invention. The design and introduction of such constructs based upon known DNA sequences is known in the art and includes such technologies as antisense RNA or DNA, co-suppression or any other such mechanism. Several of these mechanisms are described and disclosed in U.S. Pat. No. 5,686,649 to Chua et. al, which is hereby expressly incorporated herein by reference. These constructs are then introduced into plant cells using standard molecular biology techniques. The invention can be also be used for hybrid plant or seed production, once transgenic inbred parental lines have been established.

The methods of the invention described herein may be applicable to any species of plant. Resistance to one or more pathogens or diseases in a plant may be achieved directly through decreasing expression or activity of a GmUBox1 polypeptide of the present invention.

Production of a genetically modified plant tissue either expressing or inhibiting expression of a structural gene combines the teachings of the present disclosure with a variety of techniques and expedients known in the art. In most instances, alternate expedients exist for each stage of the overall process. The choice of expedients depends on the variables such as the plasmid vector system chosen for the cloning and introduction of the recombinant DNA molecule, the plant species to be modified, the particular structural gene, promoter elements and upstream elements used. Persons skilled in the art are able to select and use appropriate alternatives to achieve functionality. Culture conditions for expressing desired structural genes and cultured cells are known in the art. Also as known in the art, a number of both monocotyledonous and dicotyledonous plant species are transformable and regenerable such that whole plants containing and expressing desired genes under regulatory control of the promoter molecules according to the invention may be obtained. As is known to those of skill in the art, expression in transformed plants may be tissue specific and/or specific to certain developmental stages. Truncated promoter selection and structural gene selection are other parameters which may be optimized to achieve desired plant expression or inhibition as is known to those of skill in the art and taught herein.

V. Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8: 238 (1989). See also, U.S. Pat. No. 5,563,055, (Townsend and Thomas), issued Oct. 8, 1996.

B. Direct Gene Transfer

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559-563 (1988), Sanford, J. C., *Physiol Plant* 79: 206 (1990), Klein et al., *Biotechnology* 10: 268 (1992). See also U.S. Pat. No. 5,015,580 (Christou, et al), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al., *EMBO J.,* 4: 2731 (1985), Christou et al., *Proc Natl. Acad. Sci. U.S.A.* 84: 3962 (1987). Direct uptake of DNA into protoplasts using CaCl2 precipitation, polyvinyl alcohol or poly-L-ornithine have also been reported. Hain et al., *Mol. Gen. Genet.* 199: 161 (1985) and Draper et al., *Plant Cell Physiol.* 23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495-1505 (1992) and Spencer et al., *Plant Mol. Biol.* 24: 51-61 (1994). Following transformation of soybean target tissues, expression of the above-described selectable marker genes allows for preferential selection of transformed cells, tissues and/or plants, using regeneration and selection methods now well known in the art.

It is often desirable to have the DNA sequence in homozygous state which may require more than one transformation event to create a parental line, requiring transformation with a first and second recombinant DNA molecule both of which encode the same gene product. It is further contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques known to those of skill in the art. The transformed cells may then be regenerated into a transgenic plant. The regenerated plants are transferred to standard soil conditions and cultivated in a conventional manner. After the expression or inhibition cassette is stably incorporated into regenerated transgenic plants, it can be transferred to other plants by sexual crossing. Any of a number of standard breeding techniques can be used, depending upon the species to be crossed.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

As indicated above, it may be desirable to produce plant lines which are homozygous for a particular gene. In some species this is accomplished rather easily by the use of anther culture or isolated microspore culture. This is especially true for the oil seed crop *Brassica napus* (Keller and Armstrong, Z. flanzenzucht 80:100-108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Creation of homozygous parental lines makes possible the production of hybrid plants and seeds which will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

Transformed plant cells which are derived by any of the above transformation techniques can be cultured to regenerate a whole plant which possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. Ann. Rev. of Plant Phys. 38:467-486 (1987).

The nucleic acids of the invention can be used to confer desired traits on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Mani-* hot, *Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*. A useful plant of the invention can be a dehiscent seed plant, and a particularly useful plant of the invention can be a member of the Brassicaceae, such as rapeseed, or a member of the Fabaceae, such as a soybean, pea, lentil or bean plant.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

The following examples are offered by way of illustration and not by way of limitation.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y., (1989) and Current Protocols in Molecular Biology, F. M. Ausubel et al., eds., Current Protocols, a joint venture between Greene Publishing Associates, Inc. and John Wiley & Sons, Inc., (supplemented through 2004).

EXAMPLES

Examples

The present invention is further defined in the following Examples, in which parts and percentages are by weight and degrees are Celsius, unless otherwise stated. The disclosure of each reference set forth herein is incorporated herein by reference in its entirety.

Examples

The present invention is further defined in the following Examples, in which parts and percentages are by weight and degrees are in Celsius, unless otherwise stated. The disclosure of each reference set forth herein is incorporated herein by reference in its entirety.

Example 1

Isolation of Avr1b-Interacting Proteins

The yeast strain EGY48 (Clontech) containing the p8oZlacZ plasmid was first transformed with pLexA_Avr1b as a bait, followed by transformation with a pB42AD vector containing cDNA from a *Phytophthora sojae*-infected etiolated soybean hypocotyls library. The yeast transformants were screened on the selective medium SD/Gal/Raf/-Urd-Trp/-His with X-gal and Bu salts. Positive clones were identified by sequencing with primers pB42ADF: 5'-ccagcctct-tgctgagtggagatg-3'(SEQ ID NO:14) and pB42ADR: 5'-caaggtagacaagccgacaacc-3' (SEQ ID NO:15). There were 8 positive clones. Three of these clones encode a U-box protein.

Eight clones encoding putative Avr1b-interactors were identified from screening of the *P. sojae*-infected etiolated soybean hypocotyls library. Sequencing of these clones allowed us to classify these clones into five proteins (Table 1). GmUBox1, was selected for further study. The isolated GmUBox1 cDNA from the yeast two-hybrid screen was truncated at the N-terminus and does not contain the first 70 amino acids that contain the UBox domain. Two copies of the gene encoding the U-box protein are present in the soybean genome (FIG. 1). We named the two genes, GmUBox1-1 and GmUBox1-2. At the amino acid level, the two genes share 94% identity. Investigation of the possible colinearity in the flanking regions of the two genes suggested that they are in homologous regions of the soybean genome and evolved through duplication during the polyploidization event (FIG. 2). Sequence comparison of GmUBox1 proteins with homologous *Arabidopsis* PUB and rice SPL11 proteins revealed that U-box domain is conserved among these proteins and GmUBox1-1 is closest to *Arabidopsis* PUB23 protein (FIGS. 3 and 4).

TABLE 1

Five proteins including a U-box protein were identified as Avr1b interactors.

| Clone ID | Putative Annotation | Expected value |
|---|---|---|
| Avr1b_Inter 1 | Photosystem II reaction center PSB28 protein, chloroplast precursor | 6E−54 |
| Avr1b_Inter 3 | Unnamed protein product | 1E−55 |
| Avr1b_Inter 4 | UDP-glucose 6-dehydrogenase | 4E−55 |
| Avr1b_Inter 2 | Unknown | 4E−69 |
| Avr1b_Inter 8 | | |
| Avr1b_Inter 5 | U-box | 5E−121 |
| Avr1b_Inter 6 | | |
| Avr1b_Inter 7 | | |

Example 2

Bimolecular Fluorescence Complementation (BiFC) for Detecting Interaction of GmUBox1-1 with Avr1b in Plant Cells The protein was isolated through its interaction with *P. sojae* Avr1b protein in yeast, and we therefore determined the authenticity of the interaction in onion cells by conducting bimolecular fluorescence complementation (BiFC) assay. Same microscopic field was viewed under both red and green isothiocyanate filters (FIG. 5). BiFC analyses suggested in planta interaction between the two proteins and therefore GmUBox1-1 is most likely a true interacting protein of *P. sojae* Avr1b.

Bimolecular Fluorescence Complementation (BiFC) was Conducted as Follows:

To visualize the interaction between Avr1b protein and U-box protein in vivo, Avr1b and U-box partial sequences were PCR amplified and cloned into pSAT1-cEYFP-C1-(B)

and pSAT1-nEYFP-N1 (on the world wide web at biology.purdue.edu/people/faculty/gelvin/nsf/protocols_vectors.htm) respectively. The Avr1b sequence was amplified using the following primers (restriction sites are in bold type): 5'-GACTAAGCTTCGATGCGTCTATCTTTTGTGC-3' (SEQ ID NO:16) and 5'-AGTCGGATCCTCACTGGTGGT-GCTGGTGGTG-3' (SEQ ID NO:17) and cloned into pSAT1-cEYFP-C1-(B). The U-box core sequence was amplified using the following primers: 5'-GACTAGATCTCGATG-CAATCTTGGIGCACCCTC-3' (SEQ ID NO:18) and 5'-CAGGATCCCGGGTTCCTTTGCCCTCTCCTTAG-3' (SEQ ID NO:19) and cloned into pSAT1-nEYFP-N1. Onion lamellas were placed inside Petri plates containing moist filter papers and then bombarded with DNA coated gold particles. Gold particles were coated with either (1) pRFP, the positive control to check successful shooting or (2) U-box and Avr1b plasmids. Both categories of gold particles were mixed in equal amount before shooting. Bombarded onions were kept overnight in dark condition. The following day fluorescence microscopy was performed to monitor the possible protein-protein interaction.

Example 3

U-box Interaction with Avr1b Mutants

To identify the region of Avr1b protein that binds the GmUBox1-1 protein, we conducted yeast two-hybrid analyses of the interactions of GmUBox1-1 with Avr1b mutant proteins (FIG. 6; Dao et al. 2008). Avr1b mutants, W3, W4 and Y1 showed loss of interaction with +GmUBox1-1. The isoleucine of the W motif, mutated in W3 and W4, is conserved across most paralogous Avr1b proteins. GmUBox1-1 protein may interact with some other Avr proteins of *P. sojae* and *P. infestans*.

Yeast two-hybrid assays: Avr1b mutants (Daolong Dao et al. 2008) cloned into pLexA vector, from Dr. Brett M. Tyler (Virginia Bioinformatics Institute, Virginia Polytechnic Institute and State University, Blacksburg, Va., USA), were tested for interaction with pB42AD_U-box based on MATCH-MAKER LexA two-hybrid system (Clontech). Avr1b was used as the positive control and Lam was used as the negative control. The yeast strain EGY48 with the p8oZlacZ plasmid in it was first transformed with pB42AD_U-box, followed by transformation with Avr1b, Avr1b mutants and Lam fused in pLexA vector. The yeast transformants were screened on the selective medium SD/Gal/Raf/-Ura/-Trp/-His with X-gal and Bu salts.

Example 4

Silencing of GmUBox1 to Determine its Role in the Expression of Disease Resistance (Prophetic)

To establish the function of GmUBox1, we silenced the expression of GmUBox1 by conducting RNAi as follows.
Preparing RNAi vectors and constructs: RNAi constructs used to silence the GmUBox1-1 and GmUBox1-2 may be generated as follows. A fragment for each putative GmUBox1 will be amplified by PCR from the corresponding cDNA clones. The PCR products will be cloned in the pHannibal vector as inverted repeat which would form self-complimentary 'hairpin' RNA (hpRNA) to efficiently silence the gene. (Wesley et al., 2001). The NotI fragments from pHANNIBAL containing ihp-cDNAs will then be subcloned into the binary vector pART27:GFP. The pART27:GFP vector will be obtained by cloning the 35S:GFP from p35S-GFP (Clontech, Mountain View, Calif.) into the Sac I site of pART27 (Wesley et al., 2001). The same molecule will be cloned into pISUAgron5 binary vector for generating stable transgenic soybean plants of the invention. Each RNAi construct will be sequenced to confirm the correct orientation as inverted repeat.

Plant materials: Soybean seedlings of Williams and Williams 82 will be grown in coarse vermiculite in a Conviron Growth Chamber (22° C., 12 hour photoperiod) in the Agronomy Hall at Iowa State University. Seedlings will be watered once on day 3. On day 7 cotyledons will be harvested for *A. rhizogenes*-mediated transformation.

*Agrobacterium rhizogenes* manipulation: The *A. rhizogenes* strain K599 will be provided by Dr. Thomas Baum, Iowa State University. Empty vector pART27GFP and the vector pART27GFP harboring individual RNAi constructs will be transformed into the *A. rhizogenes* strain K599 by the freeze-thaw transformation method (An et al., 1988). Each RNAi construct and the empty vector in *A. rhizogenes* will be grown in 10 ml LB at 28° C. with shaking at 250 rpm for two days. Before inoculation of the wounded cotyledons, the cultures will be pelleted and the cells were resuspended in 10 mM MgSO4 (OD600=~0.3) (Subramanian, 2005).

*Agrobacterium rhizogenes*-mediated transformation of soybean cotyledons: A protocol of soybean cotyledon transformation with *A. rhizogenes* described by Subramanian et al. (2005) will be performed with modifications. Individual cotyledon will be first surface sterilized with North 0/H Pak alcohol wipes (North Safety Products, Cranston, R.I.). The centers of the surface-sterilized cotyledons will be wounded with a 200 μl pipette tip. The wounded cotyledons will be placed on Petri plates containing sterile Whatman filter papers (9 cm in diameter) moistened with 3.0 ml sterile ddH2O. Twenty microliter *A. rhizogenes* suspension in 10 mM MgSO4 will be added into the circular holes made in individual cotyledons. Plates will be wrapped with Parafilm and cultured at 22° C. with a 12-h light cycle of ~150 μEs light intensity.

Infection of *A. rhizogenes* transformed cotyledons with *P. sojae*: *P. sojae* isolate 997A-2-3 will be grown on lima bean agar plate in the dark at 22° C. Seven-day old *P. sojae* was used for infection. Four weeks after transformation of cotyledons with *A. rhizogenes* K599 carrying either the empty vector or individual RNAi constructs, a small piece (~2 mm×2 mm) of lima bean agar containing *P. sojae* mycellia will be placed on the site of transformation. Seventy-two hours after *P. sojae* infection, the number of susceptible and resistance cotyledons will be recorded and pictures will be taken.

*Agrobacterium tumefaciens* manipulation: For generating stable transgenic GmUBox1-silenced plants, the RNAi construct used for *A. rhizogenes*-mediated transformation will be cloned into pISUAgron5 binary vector and recombinant plasmid will transformed into *A. tumefaciens* EHA101 strain. *A. tumefaciens* carrying the RNAi construct for silencing GmUBox1 will then be used to transform soybean, which will be conducted at the ISU Plant Transformation Facility. Progenies of stable transgenic plants will tested for enhanced *Phytophthora* resistance.

Example 5

Preparing Antibodies to a GmUBox1 of the Invention (Prophetic)

Polyclonal as well as monoclonal anti-GmPUB antibodies will be generated by expressing the proteins in *E. coli* and providing the proteins to ISU Hybridoma Facility. Two antibodies may be generated (i) One for the UBox domain (against the N-terminal 70 amino acids (aa) containing the UBox domain), and (ii) the second against the 100 aa from the C-terminus of the GmUBox1protein. The antibodies will be utilized in monitoring the protein during infection with *P. sojae* as well as in characterizing the dominant mutant plants (Example 6).

Example 6

Creation and Evaluation of GmUBox1 Dominant Negative Mutants (Prophetic)

GmUBox1 protein lacking the UBox domain and E3 ligase activity in the dominant negative mutant plants will compete with the endogenous GmUBox1 wild type protein for the interacting Avr1b protein. The transgenic plants overexpressing the truncated GmUBox1-1 (aa 71-403) will be evaluated for relative expression of the endogenous GmUBox1-1 and mutant GmUBox1-1 form by using anti-UBox- and anti-GmUBox1-1-C-terminal-specific antibodies (Example 5) in Western blot analyses. Transgenic plants expressing at least 10 fold truncated GmUBox1-1 form as compared to the endogenous GmUBox1-1 will be evaluated for expression of *Phytophthora* resistance. Without wishing to be bound by this theory, it is believed that such plants will be *Phytophthora* resistant as compared to the wild type non-transgenic or empty vector transformed soybean plants because Avr1b will fail to initiate susceptibility due to lack of E3 ligase activity in the mutant version of the interacting GmUBox1 protein.

Example 7

In Vitro E3 Ligase Activity of GmUBox1 (Prophetic)

In order to establish the E3 ligase activity of GmUBox1-1 and GmUBox1-2, the genes will be cloned into an expression vector such as pRSET and expressed in *E. coli*. Expressed proteins will be purified and used for E3 ligase activity assay. Each reaction (30 mL final volume) will contain 50 mM Tris-HCl, pH 7.5, 5 mM MgCl2, 50 mM KCl, 2 mM ATP, 1 mM DTT, 10% glycerol, 10 mM phosphocreatine, 3.5 units of phosphocreatine kinase, 0.6 units of inorganic pyrophosphatase, 2 μg ubiquitin, 50 ng E1, 150 ng of E2, and 500 ng of GmUbox1 protein. The reactions will be incubated at 30° C. for 3 hours and terminated by adding 2×SDS-PAGE sample buffer and incubating at 65° C. for 5 min. The reactions will be analyzed by SDS-PAGE electrophoresis followed by protein gel blotting using anti-ubiquitin antibody and anti-Xpress antibody. A ladder will be detected in the Western blot if GmUbox has the E3 ligase activity. (Cho, S. K., Ryu, M. Y., Song, C., Kwak, J. M. and Kim, W. T. (2008), *Arabidopsis* PUB22 and PUB23 are homologous U-Box E3 ubiquitin ligases that play combinatory roles in response to drought stress, *The Plant cell*, 20, 1899-1914; Gonzalez-Lamothe, R., Tsitsigiannis, D. I., Ludwig, A. A., Panicot, M., Shirasu, K. and Jones, J. D. (2006), The U-box protein CMPG1 is required for efficient activation of defense mechanisms triggered by multiple resistance genes in tobacco and tomato, *Plant Cell*, 18, 1067-1083.)

Example 8

Localization of GmUBox1 Proteins (Prophetic)

To better understand the way GmUBox1 functions, the protein will be localized into sub-cellular compartment of plant cells as follows.

Seven day old etiolated hypocotyls lack chlorophylls and are suitable for protein localization using green fluorescence protein (GFP) as the reporter. The N- and C-terminal regions of GmUBox1 proteins will be fused to GFP for characterizing GmUBox11-1 and GmUBox11-2 (Prelim. data). The fusions of GFP with each GmUBox1 will be transiently expressed in etiolated Williams 82 hypocotyls following particle bombardment. Eighteen hours later, the hypocotyls will be inoculated with *P. sojae* races 1 or 25, or water droplets. Two and four hours after inoculation, the location of individual GmUBox1 proteins in infected and healthy control tissues will be determined by fluorescence microscopy. In some experiments, oomycete effectors that interact with the GmUBox1 proteins will be co-expressed to determine if the effector alters the level or localization of the host protein.

Example 9

Challenges with Pathogens and Changes in Expression of GmUBox1 (Prophetic)

In soybean, challenges will include infection during several time points by *Phytophthora sojae, Pseudomonas syringae* pv. *glycinea, Fusarium virguliforme* (sudden death syndrome) and *Macrophomina phaseolina*. Desiccation and flooding of seedlings will be included as abiotic stresses, for example, environmental stresses. Those experiments will be carried out with the well-characterized cultivar Williams. Additional genetic backgrounds for *P. sojae* assays will include the widely used resistance gene Rps1k (Gao, H. and Bhattacharyya, M. K. (2008), The soybean-*Phytophthora* resistance locus Rps1-k encompasses coiled coil-nucleotide binding-leucine rich repeat-like genes and repetitive sequences, *BMC Plant Biology*, 8, 29; Gao, H., Narayanan, N. N., Ellison, L. and Bhattacharyya, M. K. (2005), Two classes of highly similar coiled coil-nucleotide binding-leucine rich repeat genes isolated from the Rps1-k locus encode *Phytophthora* resistance in soybean, *Mol Plant Microbe Interact*, 18, 1035-1045), and cultivars with differing levels of quantitative resistance, namely Sloan (more susceptible), and V71-370 and Conrad (both more resistant than Williams) (Vega-Sánchez, M. E., Redinbaugh, M. G., Costanzo, S, and Dorrance, A. E. (2005), Spatial and temporal expression analysis of defense-related genes in soybean cultivars with different levels of partial resistance to *Phytophthora sojae, Physiological and Molecular Plant Pathology*, 66, 175-182; Zhou, L., Mideros, S. X., Bao, L., Hanlon, R., Arredondo, F. D., Tripathy, S., Krampis, K., Jerauld, A., Evans, C., St. Martin, S. K. et al. (2009), Infection and Genotype Remodel the Entire Soybean Transcriptome. *BMC Genomics*, In press).

In *Arabidopsis*, Columbia (Col-O) plants will be challenged with the oomycete *Hyaloperonospora arabidopsidis*, the bacterium *Pseudomonas syringae* pv. *tomato* DC3000, and the fungus *Alternaria brassicicola*. In addition to a virulent isolate of *H. arabidopsidis*, Columbia (Col-O) plants will be challenged with four avirulent isolates that are recognized by R genes present in Col-O that utilize different signal transduction pathways (RPP7, McDowell, J. M., Cuzick, A., Can, C., Beynon, J., Dangl, J. L. and Holub, E. B. (2000), Downy mildew (*Peronospora parasitica*) resistance genes in *Arabidopsis* vary in functional requirements for NDR1, EDS1, NPR1 and salicylic acid accumulation, *Plant J*, 22, 523-529; RPP2, Holt, B. F., Boyes, D. C., Ellerstrom, M., Siefers, N., Wiig, A., Kauffman, S., Grant, M. R. and Dangl, J. L. (2002), An evolutionarily conserved mediator of plant disease resistance gene function is required for normal *Arabidopsis* development (vol 2, pg 807, 2002), *Developmental Cell*, 3, 299-

299; RPP4, van der Biezen, E. A., Freddie, C. T, Kahn, K., Parker, J. E. and Jones, J. D. (2002), *Arabidopsis RPP4 is a member of the RPP5 multigene family of TIR-NB-LRR genes and confers downy mildew resistance through multiple signalling components, Plant J,* 29, 439-451; and RPP31, McDowell, J. M., Williams, S. G., Funderburg, N. T., Eulgem, T. and Dangl, J. L. (2005), Genetic Analysis of Developmentally Regulated Resistance to Downy Mildew (*Hyaloperonospora parasitica*) in *Arabidopsis thaliana. Molecular Plant-Microbe Interactions,* 18, 1226-1234).

In each case, cDNA of GmUBox1 from 2-6 time points after challenge (depending on the assay) will be assayed with gene-specific primers and SYBR green. (Udvardi, M. K., Czechowski, T. and Scheible, W.-R. (2008), Eleven Golden Rules of Quantitative RT-PCR, *The Plant cell,* 20, 1736-1737; Gutierrez, L., Mauriat, M., Pelloux, J., Bellini, C. and Van Wuytswinkel, O. (2008) Towards a Systematic Validation of References in Real-Time RT-PCR. *The Plant cell,* 20, 1734-1735). Taqman probes will be used for increased gene specificity if necessary.

Example 10

Functional Analysis of GmUBox1s Through Complementation of the *Arabidopsis* Mutants (Prophetic)

*Arabidopsis* pub22/23/24 triple mutants showing susceptibility to *H. arabidopsidis* will be transformed with GmUBox1 to determine if the soybean protein can regain the resistance against the pathogen in transformed triple mutant. These experiments will rigorously test whether GmUBox1 and PUB22/23/24 are orthologous sequences and UBox proteins are functionally conserved between species. GmUBox1-1 and GmUBox1-2 will be cloned into binary plant expression vectors (CaMv35S promoter) and transformed into *Arabidopsis* by floral dipping (Clough, S. J. and Bent, A. F. (1998), Floral dip: a simplified method for *Agrobacterium*-mediated transformation of *Arabidopsis thaliana, Plant J,* 16, 735-743; Logemann, E., Birkenbihl, R. P., Ulker, B. and Somssich, I. E. (2006), An improved method for preparing *Agrobacterium* cells that simplifies the *Arabidopsis* transformation protocol, *Plant methods,* 2, 16). Transgenic plants will be selected for Basta resistance and bred to homozygosity. At least five transgenic lines for each transgene will be challenged with *H. arabidopsidis* and analyzed. This approach is expected to delineate functionally conserved UBox1s. The results of this study will also establish the wide applicability of the GmUBox1 protein.

Example 11

Application of GmUBox1 Proteins in Creating Disease Resistant Soybean Lines (Prophetic)

The GmUBox1-1 gene identified from soybean showed high homology to PUB23. The alignment of GmUBox1-1 with PUB22, PUB23, PUB24 and SPL11 revealed high similarity of the U-box domain among these proteins. Without wishing to be bound by this theory, the putative function of GmUBox1-1 is most likely E3 ubiquitin ligase that may regulate negatively the expression of disease resistance in soybean and GmUBox1-1's target proteins is expected to be positive regulators of defense signaling pathway. Soybean cultivars with mutated novel GmUBox1 genes may provide broad-spectrum resistance against many pathogens.

Example 12

Identification of Proteins that are Ubiquitinated by GmUBox1-1 Interactors (Prophetic)

A yeast two-hybrid screen will be applied to identify soybean proteins that interact with GmUBox1-1. The GmUBox1 expressed as baits in the pLexA vector (Clontech) will be used to screen the prey cDNA library from *P. sojae*-infected tissues in p42Ad vector (Clontech). Candidate interacting proteins will be confirmed by conducting in vitro and in vivo interaction studies. Candidate GmUBox1-interactor genes will be silenced by RNAi method described earlier in Example 4. Without wishing to be bound by this theory, GmUBox1-interacting genes may be master regulators of disease resistance and therefore their manipulation will result in broad-spectrum disease resistance in transgenic soybean lines.

What is claimed is:

1. An isolated nucleic acid molecule, wherein said nucleic acid molecule comprises,
a polynucleotide sequence selected from the group consisting of:
   (a) a polynucleotide sequence comprising the sequence set forth in SEQ ID NOS: 1 or 2;
   (b) a polynucleotide sequence having at least 95% sequence identity to the sequence of SEQ ID NOS: 1 or 2, wherein said nucleotide sequence encodes a GmUBox1 polypeptide;
   (c) a nucleic acid molecule comprising a full length complement of SEQ ID NOS: 1 or 2;
   (d) a polynucleotide sequence comprising a sequence encoding the amino acid sequence set forth in SEQ ID NOS: 3; or
   (e) a sequence which hybridizes under highly stringent conditions to the lull length of the polynucleotide of any of (a) through (d) wherein said sequence encodes a GmUBox1 polypeptide.

2. The nucleic acid of claim 1 wherein the nucleic acid encodes a GmUBox1 protein having GmUBox1 activity selected from the group consisting of: (a) E3 ubiquitin ligase activity, (b) conferring in a plant susceptibility to a plant pathogen, (c) conferring in a plant susceptibility to an environmental stress, or (d) protein-protein interaction with an Avr1b.

3. A vector comprising the nucleic acid of claim 1.

4. An expression cassette comprising the nucleic acid of claim 1.

5. The expression cassette of claim 4, wherein the nucleic acid is oriented in the antisense direction.

6. The nucleic acid molecule of claim 1 wherein said molecule is a soybean nucleic acid.

7. A plant cell comprising the nucleic acid of claim 1.

8. The plant cell of claim 7, wherein the plant cell is from a monocotyledonous plant.

9. The plant cell of claim 7, wherein the plant cell is from a dicotyledonous plant.

* * * * *